US012758229B2

(12) United States Patent
Becking et al.

(10) Patent No.: US 12,758,229 B2
(45) Date of Patent: Oct. 13, 2026

(54) MULTIPLE LAYER FILAMENTARY DEVICES FOR TREATMENT OF VASCULAR DEFECTS

(71) Applicant: Covidien LP, Mansfield, MA (US)

(72) Inventors: Frank Becking, Santa Clara, CA (US); Arturo Rosqueta, San Jose, CA (US)

(73) Assignee: Covidien LP, Mansfield, MA (US)

(*) Notice: Subject to any disclaimer, the term of this patent is extended or adjusted under 35 U.S.C. 154(b) by 929 days.

(21) Appl. No.: 16/893,431

(22) Filed: Jun. 4, 2020

(65) Prior Publication Data

US 2020/0367904 A1 Nov. 26, 2020

Related U.S. Application Data

(63) Continuation of application No. 15/415,669, filed on Jan. 25, 2017, now abandoned, which is a (Continued)

(51) Int. Cl.
*A61B 17/00* (2006.01)
*A61B 17/12* (2006.01)
(Continued)

(52) U.S. Cl.
CPC .. *A61B 17/12159* (2013.01); *A61B 17/12022* (2013.01); *A61B 17/12031* (2013.01); *A61B 17/12109* (2013.01); *A61B 17/12113* (2013.01); *A61B 17/12118* (2013.01); *A61B 17/1215* (2013.01); *A61B 17/12172* (2013.01); *A61M 29/02* (2013.01); *A61B 2017/00526* (2013.01); *A61B 2017/00862* (2013.01);
(Continued)

(58) Field of Classification Search
CPC ........ A61B 17/12002; A61B 17/12031; A61B 17/12109; A61B 17/12113; A61B 17/1215; A61B 17/12159; A61B 17/12172
USPC .......................................................... 606/200
See application file for complete search history.

(56) References Cited

U.S. PATENT DOCUMENTS

| | | | |
|---|---|---|---|
| 3,108,593 | A | 10/1963 | Glassman |
| 4,425,908 | A | 1/1984 | Simon |

(Continued)

FOREIGN PATENT DOCUMENTS

| | | | |
|---|---|---|---|
| CA | 2607529 A1 | 4/2008 | |
| CN | 101472537 A | 7/2009 | |

(Continued)

OTHER PUBLICATIONS

Ronnen, "Amplatzer Vascular Plug Case Study, Closure of Arteriovenous Fistula Between Deep Femoral Artery and Superficial Femoral Vein," AGA Medical Corporation, May 2007.

(Continued)

*Primary Examiner* — Martin T Ton
(74) *Attorney, Agent, or Firm* — Fortem IP LLP

(57) ABSTRACT

Braid-balls suitable for aneurysm occlusion and/or parent vessel occlusion/sacrifice (e.g., in treating neurovascular defects) are disclosed. Especially for aneurysm treatment, but also for either one of the aforementioned treatments, the form of the ball is very important. In particular, the density of the device is paramount in applications where braid itself is intended to moderate or stop blood flow—allowing thrombosis within a volume formed by the ball.

14 Claims, 17 Drawing Sheets

Related U.S. Application Data continuation of application No. 13/470,013, filed on May 11, 2012, now Pat. No. 9,585,669, which is a continuation of application No. 12/911,034, filed on Oct. 25, 2010, now Pat. No. 9,039,726, which is a continuation of application No. 12/427,620, filed on Apr. 21, 2009, now Pat. No. 8,142,456.

(60) Provisional application No. 61/145,097, filed on Jan. 15, 2009, provisional application No. 61/083,961, filed on Jul. 28, 2008, provisional application No. 61/083,957, filed on Jul. 28, 2008, provisional application No. 61/046,670, filed on Apr. 21, 2008, provisional application No. 61/046,594, filed on Apr. 21, 2008.

(51) Int. Cl.
*A61M 29/02* (2006.01)
*A61B 18/00* (2006.01)
*A61B 90/00* (2016.01)

(52) U.S. Cl.
CPC ............... *A61B 2017/00867* (2013.01); *A61B 2017/1205* (2013.01); *A61B 2017/12054* (2013.01); *A61B 2017/12068* (2013.01); *A61B 2018/00416* (2013.01); *A61B 2090/3966* (2016.02); *Y10T 156/1051* (2015.01)

(56) References Cited

U.S. PATENT DOCUMENTS 4,619,246 A 10/1986 Molgaard-nielsen et al.
4,655,771 A 4/1987 Wallsten
4,768,507 A 9/1988 Fischell et al.
4,921,484 A 5/1990 Hillstead
4,998,539 A 3/1991 Delsanti
5,026,377 A 6/1991 Burton et al.
5,061,275 A 10/1991 Wallsten et al.
5,064,435 A 11/1991 Porter
5,104,404 A 4/1992 Wolff
5,122,136 A 6/1992 Guglielmi et al.
5,158,548 A 10/1992 Lau et al.
5,222,971 A 6/1993 Willard et al.
5,250,071 A 10/1993 Palermo
5,284,488 A 2/1994 Sideris
5,326,350 A 7/1994 Li
5,334,210 A 8/1994 Gianturco
5,354,295 A 10/1994 Guglielmi et al.
5,378,239 A 1/1995 Termin et al.
5,405,379 A 4/1995 Lane
5,417,708 A 5/1995 Hall et al.
5,425,984 A 6/1995 Kennedy et al.
5,499,981 A 3/1996 Kordis
5,527,338 A 6/1996 Purdy
5,545,208 A 8/1996 Wolff et al.
5,545,209 A 8/1996 Roberts et al.
5,549,635 A 8/1996 Solar
5,624,461 A 4/1997 Mariant
5,634,942 A 6/1997 Chevillon et al.
5,645,558 A * 7/1997 Horton ............ A61B 17/12172 606/198
5,662,703 A 9/1997 Yurek et al.
5,669,931 A 9/1997 Kupiecki et al.
5,690,671 A 11/1997 Mcgurk et al.
5,702,419 A 12/1997 Berry et al.
5,713,907 A 2/1998 Wholey et al.
5,725,552 A 3/1998 Kotula et al.
5,728,906 A 3/1998 Eguchi et al.
5,733,294 A 3/1998 Forber et al.
5,741,333 A 4/1998 Frid
5,749,891 A 5/1998 Ken et al.
5,749,895 A 5/1998 Sawyer et al.
5,749,919 A 5/1998 Blanc
5,749,920 A 5/1998 Quiachon et al.
5,766,151 A 6/1998 Valley et al.
5,814,062 A 9/1998 Sepetka et al.
5,823,198 A 10/1998 Jones et al.
5,830,230 A 11/1998 Berryman et al.
5,846,261 A * 12/1998 Kotula ............ A61B 17/12122 606/213
5,853,422 A 12/1998 Huebsch et al.
5,855,578 A 1/1999 Guglielmi et al.
5,879,366 A 3/1999 Shaw et al.
5,908,435 A 6/1999 Samuels
5,911,731 A 6/1999 Pham et al.
5,916,235 A 6/1999 Guglielmi
5,925,060 A * 7/1999 Forber ............ A61B 17/12109 606/191
5,928,228 A 7/1999 Kordis et al.
5,928,260 A 7/1999 Chin et al.
5,935,148 A 8/1999 Villar et al.
5,935,362 A 8/1999 Petrick
5,941,249 A 8/1999 Maynard
5,944,738 A 8/1999 Amplatz et al.
5,951,599 A 9/1999 Mccrory
5,957,948 A 9/1999 Mariant
5,964,797 A 10/1999 Ho
5,976,162 A 11/1999 Doan et al.
5,976,169 A 11/1999 Imran
5,980,554 A 11/1999 Lenker et al.
6,001,092 A 12/1999 Mirigian et al.
6,010,517 A 1/2000 Baccaro
6,022,374 A 2/2000 Imran
6,024,756 A 2/2000 Huebsch et al.
6,033,423 A 3/2000 Ken et al.
6,036,720 A 3/2000 Abrams et al.
6,059,813 A 5/2000 Vrba et al.
6,063,070 A 5/2000 Eder
6,063,104 A 5/2000 Villar et al.
6,086,577 A 7/2000 Ken et al.
6,090,125 A 7/2000 Horton
6,093,199 A 7/2000 Brown et al.
6,096,021 A 8/2000 Helm et al.
6,096,034 A 8/2000 Kupiecki et al.
6,096,073 A 8/2000 Webster et al.
6,099,526 A 8/2000 Whayne et al.
6,106,530 A 8/2000 Harada
6,110,191 A 8/2000 Dehdashtian et al.
6,123,715 A 9/2000 Amplatz
6,139,564 A 10/2000 Teoh
6,152,144 A 11/2000 Lesh et al.
6,159,531 A 12/2000 Dang et al.
6,165,193 A 12/2000 Greene et al.
6,168,592 B1 1/2001 Kupiecki et al.
6,168,615 B1 1/2001 Ken et al.
6,168,618 B1 1/2001 Frantzen
6,168,622 B1 1/2001 Mazzocchi
6,183,495 B1 2/2001 Lenker et al.
6,190,402 B1 2/2001 Horton et al.
6,193,708 B1 2/2001 Ken et al.
6,221,086 B1 4/2001 Forber
6,238,403 B1 5/2001 Greene et al.
6,261,305 B1 7/2001 Marotta et al.
6,280,412 B1 8/2001 Pederson, Jr. et al.
6,299,619 B1 10/2001 Greene et al.
6,306,141 B1 10/2001 Jervis
6,309,367 B1 10/2001 Boock
6,322,576 B1 11/2001 Wallace et al.
6,325,820 B1 12/2001 Khosravi et al.
6,331,184 B1 12/2001 Abrams
6,332,576 B1 12/2001 Colley et al.
6,342,068 B1 1/2002 Thompson
6,344,041 B1 2/2002 Kupiecki et al.
6,344,048 B1 2/2002 Chin et al.
6,346,117 B1 2/2002 Greenhalgh
6,350,270 B1 2/2002 Roue
6,361,558 B1 3/2002 Hieshima et al.
6,364,895 B1 4/2002 Greenhalgh
6,368,339 B1 4/2002 Amplatz
6,371,980 B1 4/2002 Rudakov et al.
6,375,668 B1 4/2002 Gifford et al.
6,379,372 B1 4/2002 Dehdashtian et al.

(56) References Cited

U.S. PATENT DOCUMENTS 6,383,174 B1 5/2002 Eder
6,391,037 B1 5/2002 Greenhalgh
6,409,750 B1 6/2002 Hyodoh et al.
6,428,558 B1 * 8/2002 Jones ............... A61B 17/12022 606/151
6,443,972 B1 9/2002 Bosma et al.
6,447,531 B1 9/2002 Amplatz
6,451,050 B1 9/2002 Rudakov et al.
6,454,780 B1 9/2002 Wallace
6,494,884 B2 12/2002 Gifford et al.
6,506,204 B2 1/2003 Mazzocchi
6,511,468 B1 1/2003 Cragg et al.
6,530,934 B1 3/2003 Jacobsen et al.
6,544,278 B1 4/2003 Vrba et al.
6,547,804 B2 4/2003 Porter et al.
6,551,303 B1 4/2003 Van Tassel et al.
6,569,179 B2 5/2003 Teoh et al.
6,579,302 B2 6/2003 Duerig et al.
6,579,303 B2 6/2003 Amplatz
6,585,748 B1 7/2003 Jeffree
6,585,756 B1 7/2003 Strecker
6,589,256 B2 7/2003 Forber
6,589,265 B1 7/2003 Palmer et al.
6,591,472 B1 7/2003 Noone et al.
6,592,605 B2 7/2003 Lenker et al.
6,599,308 B2 7/2003 Amplatz
6,602,261 B2 8/2003 Greene, Jr. et al.
6,605,101 B1 8/2003 Schaefer et al.
6,605,102 B1 8/2003 Mazzocchi et al.
6,605,111 B2 8/2003 Bose et al.
6,607,551 B1 8/2003 Sullivan et al.
6,613,074 B1 9/2003 Mitelberg et al.
6,626,939 B1 9/2003 Burnside et al.
6,632,241 B1 10/2003 Hancock et al.
6,635,068 B1 10/2003 Dubrul et al.
6,635,069 B1 10/2003 Teoh et al.
6,652,555 B1 11/2003 Vantassel et al.
6,652,556 B1 11/2003 Vantassel et al.
6,666,882 B1 12/2003 Bose et al.
6,666,883 B1 12/2003 Seguin et al.
6,669,717 B2 12/2003 Marotta et al.
6,669,721 B1 12/2003 Bose et al.
6,676,696 B1 1/2004 Marotta et al.
6,682,505 B2 1/2004 Bates et al.
6,682,546 B2 1/2004 Amplatz
6,689,150 B1 2/2004 Vantassel et al.
6,689,486 B2 2/2004 Ho et al.
6,695,876 B1 2/2004 Marotta et al.
6,698,877 B2 3/2004 Urlaub et al.
6,699,274 B2 3/2004 Stinson
6,709,465 B2 3/2004 Mitchell et al.
6,712,835 B2 3/2004 Mazzocchi et al.
6,723,112 B2 4/2004 Ho et al.
6,723,116 B2 4/2004 Taheri
6,730,108 B2 5/2004 Van Tassel et al.
6,746,468 B1 6/2004 Sepetka et al.
6,746,890 B2 6/2004 Gupta et al.
6,780,196 B2 8/2004 Chin et al.
6,792,979 B2 9/2004 Konya et al.
6,797,083 B2 9/2004 Peterson
6,802,851 B2 10/2004 Jones et al.
RE38,653 E 11/2004 Igaki et al.
6,811,560 B2 11/2004 Jones et al.
6,855,153 B2 2/2005 Saadat
6,855,154 B2 2/2005 Abdel-gawwad
RE38,711 E 3/2005 Igaki et al.
6,860,893 B2 3/2005 Wallace et al.
6,878,384 B2 4/2005 Cruise et al.
6,905,503 B2 6/2005 Gifford et al.
6,936,055 B1 8/2005 Ken et al.
6,949,103 B2 9/2005 Mazzocchi et al.
6,949,113 B2 9/2005 Van Tassel et al.
6,953,472 B2 10/2005 Palmer et al.
6,979,341 B2 12/2005 Scribner et al.
6,989,019 B2 1/2006 Mazzocchi et al.
6,991,617 B2 1/2006 Hektner et al.
6,994,092 B2 2/2006 Van Der Burg et al.
6,994,717 B2 2/2006 Konya et al.
7,011,671 B2 3/2006 Welch
7,014,645 B2 3/2006 Greene et al.
7,018,401 B1 3/2006 Hyodoh et al.
7,029,487 B2 4/2006 Greene, Jr. et al.
7,029,949 B2 4/2006 Farnworth et al.
7,033,375 B2 4/2006 Mazzocchi et al.
7,048,752 B2 5/2006 Mazzocchi et al.
7,063,679 B2 6/2006 Maguire et al.
7,070,607 B2 7/2006 Murayama et al.
7,070,609 B2 7/2006 West
7,083,632 B2 8/2006 Avellanet et al.
7,128,073 B1 10/2006 Van Der Burg et al.
7,128,736 B1 10/2006 Abrams et al.
7,153,323 B1 12/2006 Teoh et al.
7,169,177 B2 1/2007 Obara
7,195,636 B2 3/2007 Avellanet et al.
7,211,109 B2 5/2007 Thompson
7,229,461 B2 6/2007 Chin et al.
7,232,461 B2 6/2007 Ramer
7,244,267 B2 7/2007 Huter et al.
7,261,720 B2 8/2007 Stevens et al.
7,303,571 B2 12/2007 Makower et al.
7,306,622 B2 12/2007 Jones et al.
7,326,225 B2 2/2008 Ferrera et al.
7,331,980 B2 2/2008 Dubrul et al.
7,367,985 B2 5/2008 Mazzocchi et al.
7,367,986 B2 5/2008 Mazzocchi et al.
7,371,250 B2 5/2008 Mazzocchi et al.
7,393,358 B2 7/2008 Malewicz
7,404,820 B2 7/2008 Mazzocchi et al.
7,410,482 B2 8/2008 Murphy et al.
7,410,492 B2 8/2008 Mazzocchi et al.
7,413,622 B2 8/2008 Peterson
7,419,503 B2 9/2008 Pulnev et al.
7,442,200 B2 10/2008 Mazzocchi et al.
7,481,821 B2 1/2009 Fogarty et al.
7,485,088 B2 2/2009 Murphy et al.
7,491,214 B2 2/2009 Greene et al.
7,556,635 B2 7/2009 Mazzocchi et al.
7,566,338 B2 7/2009 Mazzocchi et al.
7,569,066 B2 8/2009 Gerberding et al.
7,572,273 B2 8/2009 Mazzocchi et al.
7,572,288 B2 8/2009 Cox
7,575,590 B2 8/2009 Watson
7,597,704 B2 10/2009 Frazier et al.
7,601,160 B2 10/2009 Richter
7,608,088 B2 10/2009 Jones et al.
7,621,928 B2 11/2009 Thramann et al.
7,632,296 B2 12/2009 Malewicz
7,670,355 B2 3/2010 Mazzocchi et al.
7,670,356 B2 3/2010 Mazzocchi et al.
7,678,130 B2 3/2010 Mazzocchi et al.
7,682,390 B2 3/2010 Seguin
7,691,124 B2 4/2010 Balgobin
7,695,488 B2 4/2010 Berenstein et al.
7,699,056 B2 4/2010 Tran et al.
7,708,754 B2 5/2010 Balgobin et al.
7,727,189 B2 6/2010 Vantassel et al.
7,744,583 B2 6/2010 Seifert et al.
7,744,652 B2 6/2010 Morsi
7,763,011 B2 7/2010 Ortiz et al.
7,828,815 B2 11/2010 Mazzocchi et al.
7,828,816 B2 11/2010 Mazzocchi et al.
7,922,732 B2 4/2011 Mazzocchi et al.
7,955,343 B2 6/2011 Makower et al.
7,972,359 B2 7/2011 Kreidler
7,976,527 B2 7/2011 Cragg et al.
RE42,625 E 8/2011 Guglielmi
7,993,364 B2 8/2011 Morsi
RE42,758 E 9/2011 Ken et al.
8,012,210 B2 9/2011 Lin et al.
8,016,869 B2 9/2011 Nikolchev
8,016,872 B2 9/2011 Parker
8,043,326 B2 10/2011 Hancock et al.
8,062,379 B2 11/2011 Morsi
8,075,585 B2 12/2011 Lee et al.

(56) References Cited

U.S. PATENT DOCUMENTS

| | | | |
|---|---|---|---|
| 8,137,293 | B2 | 3/2012 | Zhou et al. |
| 8,142,456 | B2 | 3/2012 | Rosqueta et al. |
| 8,202,280 | B2 | 6/2012 | Richter |
| 8,211,160 | B2 | 7/2012 | Garrison et al. |
| 8,221,445 | B2 | 7/2012 | Van Tassel et al. |
| 8,261,648 | B1 | 9/2012 | Marchand et al. |
| 8,298,257 | B2 | 10/2012 | Sepetka et al. |
| 8,333,783 | B2 | 12/2012 | Braun et al. |
| 8,343,167 | B2 | 1/2013 | Henson |
| 8,361,104 | B2 | 1/2013 | Jones et al. |
| 8,361,138 | B2 | 1/2013 | Adams |
| 8,398,670 | B2 | 3/2013 | Amplatz et al. |
| 8,425,541 | B2 | 4/2013 | Masters et al. |
| 8,430,012 | B1 | 4/2013 | Marchand et al. |
| 8,454,681 | B2 | 6/2013 | Holman et al. |
| 8,470,013 | B2 | 6/2013 | Duggal et al. |
| 8,597,320 | B2 | 12/2013 | Sepetka et al. |
| 8,603,128 | B2 | 12/2013 | Greene et al. |
| 8,715,317 | B1 | 5/2014 | Janardhan et al. |
| 8,834,515 | B2 | 9/2014 | Win et al. |
| 8,906,057 | B2 | 12/2014 | Connor et al. |
| 8,974,512 | B2 | 3/2015 | Aboytes et al. |
| 8,998,947 | B2 | 4/2015 | Aboytes et al. |
| 9,211,202 | B2 | 12/2015 | Strother et al. |
| 9,301,769 | B2 | 4/2016 | Brady et al. |
| 9,314,248 | B2 | 4/2016 | Molaei |
| 9,486,224 | B2 | 11/2016 | Riina et al. |
| 9,629,636 | B2 | 4/2017 | Fogarty et al. |
| 9,833,309 | B2 | 12/2017 | Levi et al. |
| 9,844,380 | B2 | 12/2017 | Furey |
| 9,907,684 | B2 | 3/2018 | Connor et al. |
| 9,962,146 | B2 | 5/2018 | Hebert et al. |
| 10,028,745 | B2 | 7/2018 | Morsi |
| 2001/0000797 | A1* | 5/2001 | Mazzocchi ...... A61B 17/12177 606/151 |
| 2001/0001835 | A1 | 5/2001 | Greene et al. |
| 2001/0007082 | A1 | 7/2001 | Dusbabek et al. |
| 2001/0012949 | A1 | 8/2001 | Forber |
| 2001/0051822 | A1 | 12/2001 | Stack et al. |
| 2002/0013599 | A1 | 1/2002 | Limon et al. |
| 2002/0013618 | A1 | 1/2002 | Marotta et al. |
| 2002/0026210 | A1 | 2/2002 | Abdel-Gawwad |
| 2002/0042628 | A1 | 4/2002 | Chin et al. |
| 2002/0062091 | A1 | 5/2002 | Jacobsen et al. |
| 2002/0062145 | A1 | 5/2002 | Rudakov et al. |
| 2002/0111647 | A1 | 8/2002 | Khairkhahan et al. |
| 2002/0119177 | A1 | 8/2002 | Bowman et al. |
| 2002/0147462 | A1 | 10/2002 | Mair et al. |
| 2002/0165572 | A1 | 11/2002 | Saadat |
| 2002/0169473 | A1 | 11/2002 | Sepetka et al. |
| 2002/0193812 | A1 | 12/2002 | Patel et al. |
| 2002/0193813 | A1 | 12/2002 | Helkowski et al. |
| 2003/0004533 | A1 | 1/2003 | Dieck et al. |
| 2003/0004538 | A1 | 1/2003 | Secrest et al. |
| 2003/0004568 | A1 | 1/2003 | Ken et al. |
| 2003/0018294 | A1 | 1/2003 | Cox |
| 2003/0028209 | A1 | 2/2003 | Teoh et al. |
| 2003/0040772 | A1 | 2/2003 | Hyodoh et al. |
| 2003/0055440 | A1 | 3/2003 | Jones et al. |
| 2003/0057156 | A1 | 3/2003 | Peterson et al. |
| 2003/0093111 | A1 | 5/2003 | Ken et al. |
| 2003/0113478 | A1 | 6/2003 | Dang et al. |
| 2003/0114918 | A1 | 6/2003 | Garrison et al. |
| 2003/0149490 | A1 | 8/2003 | Ashman |
| 2003/0171739 | A1 | 9/2003 | Murphy et al. |
| 2003/0171770 | A1 | 9/2003 | Kusleika et al. |
| 2003/0176884 | A1 | 9/2003 | Berrada et al. |
| 2003/0187473 | A1 | 10/2003 | Berenstein et al. |
| 2003/0195553 | A1 | 10/2003 | Wallace et al. |
| 2003/0199913 | A1 | 10/2003 | Dubrul et al. |
| 2003/0199919 | A1 | 10/2003 | Palmer et al. |
| 2003/0212419 | A1 | 11/2003 | West |
| 2004/0015224 | A1 | 1/2004 | Armstrong et al. |
| 2004/0034386 | A1 | 2/2004 | Fulton et al. |
| 2004/0044361 | A1 | 3/2004 | Frazier et al. |
| 2004/0044391 | A1 | 3/2004 | Porter |
| 2004/0064093 | A1 | 4/2004 | Hektner et al. |
| 2004/0098027 | A1 | 5/2004 | Teoh et al. |
| 2004/0098030 | A1 | 5/2004 | Makower et al. |
| 2004/0106945 | A1 | 6/2004 | Thramann et al. |
| 2004/0106977 | A1 | 6/2004 | Sullivan et al. |
| 2004/0111112 | A1 | 6/2004 | Hoffmann |
| 2004/0115164 | A1 | 6/2004 | Pierce et al. |
| 2004/0122467 | A1 | 6/2004 | Vantassel et al. |
| 2004/0122468 | A1 | 6/2004 | Yodfat et al. |
| 2004/0138758 | A1 | 7/2004 | Kronengold et al. |
| 2004/0143239 | A1 | 7/2004 | Zhou et al. |
| 2004/0143286 | A1 | 7/2004 | Johnson et al. |
| 2004/0153119 | A1 | 8/2004 | Kusleika et al. |
| 2004/0161451 | A1 | 8/2004 | Pierce et al. |
| 2004/0162606 | A1 | 8/2004 | Thompson |
| 2004/0172056 | A1 | 9/2004 | Guterman et al. |
| 2004/0172121 | A1 | 9/2004 | Eidenschink et al. |
| 2004/0181253 | A1 | 9/2004 | Sepetka et al. |
| 2004/0186562 | A1 | 9/2004 | Cox |
| 2004/0193206 | A1 | 9/2004 | Gerberding et al. |
| 2004/0215229 | A1 | 10/2004 | Coyle |
| 2004/0215332 | A1 | 10/2004 | Frid |
| 2004/0249408 | A1 | 12/2004 | Murphy et al. |
| 2004/0267346 | A1 | 12/2004 | Shelso |
| 2005/0010281 | A1 | 1/2005 | Yodfat et al. |
| 2005/0021077 | A1 | 1/2005 | Chin et al. |
| 2005/0033408 | A1 | 2/2005 | Jones et al. |
| 2005/0033409 | A1 | 2/2005 | Burke et al. |
| 2005/0049625 | A1 | 3/2005 | Shaya et al. |
| 2005/0060017 | A1 | 3/2005 | Fischell et al. |
| 2005/0096728 | A1 | 5/2005 | Ramer |
| 2005/0096732 | A1 | 5/2005 | Marotta et al. |
| 2005/0107823 | A1 | 5/2005 | Leone et al. |
| 2005/0131443 | A1 | 6/2005 | Abdel-gawwad |
| 2005/0222580 | A1 | 10/2005 | Gifford et al. |
| 2005/0222605 | A1 | 10/2005 | Greenhalgh et al. |
| 2005/0228434 | A1* | 10/2005 | Amplatz .......... A61B 17/12109 606/200 |
| 2005/0267510 | A1 | 12/2005 | Razack |
| 2005/0267511 | A1 | 12/2005 | Marks et al. |
| 2005/0267527 | A1 | 12/2005 | Sandoval et al. |
| 2005/0267568 | A1 | 12/2005 | Berez et al. |
| 2005/0273135 | A1 | 12/2005 | Chanduszko et al. |
| 2005/0277978 | A1 | 12/2005 | Greenhalgh |
| 2005/0278023 | A1 | 12/2005 | Zwirkoski |
| 2005/0288763 | A1 | 12/2005 | Andreas et al. |
| 2006/0034883 | A1 | 2/2006 | Dang et al. |
| 2006/0052816 | A1 | 3/2006 | Bates et al. |
| 2006/0064151 | A1 | 3/2006 | Guterman et al. |
| 2006/0074475 | A1 | 4/2006 | Gumm |
| 2006/0106421 | A1 | 5/2006 | Teoh |
| 2006/0116709 | A1 | 6/2006 | Sepetka et al. |
| 2006/0116712 | A1 | 6/2006 | Sepetka et al. |
| 2006/0116713 | A1 | 6/2006 | Sepetka et al. |
| 2006/0116714 | A1 | 6/2006 | Sepetka et al. |
| 2006/0122548 | A1 | 6/2006 | Abrams |
| 2006/0155323 | A1 | 7/2006 | Porter et al. |
| 2006/0167494 | A1 | 7/2006 | Suddaby |
| 2006/0190070 | A1 | 8/2006 | Dieck et al. |
| 2006/0190076 | A1 | 8/2006 | Taheri |
| 2006/0200221 | A1 | 9/2006 | Malewicz |
| 2006/0200234 | A1 | 9/2006 | Hines |
| 2006/0206140 | A1 | 9/2006 | Shaolian et al. |
| 2006/0206198 | A1 | 9/2006 | Churchwell et al. |
| 2006/0206199 | A1 | 9/2006 | Churchwell et al. |
| 2006/0206200 | A1 | 9/2006 | Garcia et al. |
| 2006/0217799 | A1 | 9/2006 | Mailänder et al. |
| 2006/0224183 | A1* | 10/2006 | Freudenthal ..... A61B 17/12036 606/213 |
| 2006/0229700 | A1 | 10/2006 | Acosta et al. |
| 2006/0235464 | A1 | 10/2006 | Avellanet et al. |
| 2006/0235501 | A1 | 10/2006 | Igaki |
| 2006/0241686 | A1 | 10/2006 | Ferrera et al. |
| 2006/0241690 | A1 | 10/2006 | Amplatz et al. |
| 2006/0247680 | A1 | 11/2006 | Amplatz et al. |
| 2006/0264905 | A1 | 11/2006 | Eskridge et al. |
| 2006/0264907 | A1 | 11/2006 | Eskridge et al. |
| 2006/0271149 | A1 | 11/2006 | Berez et al. |

(56) References Cited

U.S. PATENT DOCUMENTS

| | | | | |
|---|---|---|---|---|
| 2006/0271153 | A1 | 11/2006 | Garcia et al. | |
| 2006/0271162 | A1 | 11/2006 | Vito et al. | |
| 2006/0282152 | A1 | 12/2006 | Beyerlein et al. | |
| 2006/0292206 | A1 | 12/2006 | Kim et al. | |
| 2006/0293744 | A1 | 12/2006 | Peckham et al. | |
| 2007/0003594 | A1 | 1/2007 | Brady et al. | |
| 2007/0005125 | A1 | 1/2007 | Berenstein et al. | |
| 2007/0010850 | A1 | 1/2007 | Balgobin et al. | |
| 2007/0014831 | A1 | 1/2007 | Sung et al. | |
| 2007/0016243 | A1 | 1/2007 | Ramaiah et al. | |
| 2007/0021816 | A1 | 1/2007 | Rudin | |
| 2007/0050017 | A1 | 3/2007 | Sims et al. | |
| 2007/0083226 | A1 | 4/2007 | Buiser et al. | |
| 2007/0088387 | A1 | 4/2007 | Eskridge et al. | |
| 2007/0093889 | A1 | 4/2007 | Wu et al. | |
| 2007/0100415 | A1 | 5/2007 | Licata et al. | |
| 2007/0100426 | A1 | 5/2007 | Rudakov et al. | |
| 2007/0106311 | A1 | 5/2007 | Wallace et al. | |
| 2007/0135826 | A1 | 6/2007 | Zaver et al. | |
| 2007/0135907 | A1 | 6/2007 | Wilson et al. | |
| 2007/0150045 | A1 | 6/2007 | Ferrera | |
| 2007/0162104 | A1 | 7/2007 | Frid | |
| 2007/0167876 | A1 | 7/2007 | Euteneuer et al. | |
| 2007/0167877 | A1 | 7/2007 | Euteneuer et al. | |
| 2007/0167972 | A1 | 7/2007 | Euteneuer et al. | |
| 2007/0167980 | A1* | 7/2007 | Figulla | A61B 17/12177 606/213 |
| 2007/0173928 | A1 | 7/2007 | Morsi | |
| 2007/0175536 | A1 | 8/2007 | Monetti et al. | |
| 2007/0179520 | A1 | 8/2007 | West | |
| 2007/0185442 | A1 | 8/2007 | Euteneuer et al. | |
| 2007/0185443 | A1 | 8/2007 | Euteneuer et al. | |
| 2007/0185444 | A1 | 8/2007 | Euteneuer et al. | |
| 2007/0185457 | A1 | 8/2007 | Euteneuer et al. | |
| 2007/0191884 | A1 | 8/2007 | Eskridge et al. | |
| 2007/0191924 | A1 | 8/2007 | Rudakov | |
| 2007/0198059 | A1 | 8/2007 | Patel et al. | |
| 2007/0198075 | A1 | 8/2007 | Levy | |
| 2007/0203567 | A1 | 8/2007 | Levy | |
| 2007/0219619 | A1 | 9/2007 | Dieck et al. | |
| 2007/0221230 | A1 | 9/2007 | Thompson et al. | |
| 2007/0225760 | A1 | 9/2007 | Moszner et al. | |
| 2007/0225794 | A1 | 9/2007 | Thramann et al. | |
| 2007/0233224 | A1 | 10/2007 | Leynov et al. | |
| 2007/0233244 | A1 | 10/2007 | Lopez et al. | |
| 2007/0239261 | A1 | 10/2007 | Bose et al. | |
| 2007/0265656 | A1 | 11/2007 | Amplatz et al. | |
| 2007/0270902 | A1 | 11/2007 | Slazas et al. | |
| 2007/0276426 | A1 | 11/2007 | Euteneuer | |
| 2007/0276427 | A1 | 11/2007 | Euteneuer | |
| 2007/0282373 | A1 | 12/2007 | Ashby et al. | |
| 2007/0288083 | A1 | 12/2007 | Hines | |
| 2007/0293935 | A1 | 12/2007 | Olsen et al. | |
| 2008/0009934 | A1 | 1/2008 | Schneider et al. | |
| 2008/0021535 | A1 | 1/2008 | Leopold et al. | |
| 2008/0033366 | A1 | 2/2008 | Matson et al. | |
| 2008/0039933 | A1 | 2/2008 | Yodfat et al. | |
| 2008/0045996 | A1 | 2/2008 | Makower et al. | |
| 2008/0045997 | A1 | 2/2008 | Balgobin et al. | |
| 2008/0051705 | A1 | 2/2008 | Von Oepen et al. | |
| 2008/0058856 | A1 | 3/2008 | Ramaiah et al. | |
| 2008/0065141 | A1 | 3/2008 | Holman et al. | |
| 2008/0065145 | A1 | 3/2008 | Carpenter | |
| 2008/0081763 | A1 | 4/2008 | Swetlin et al. | |
| 2008/0082176 | A1 | 4/2008 | Slazas | |
| 2008/0086196 | A1 | 4/2008 | Truckai et al. | |
| 2008/0097495 | A1 | 4/2008 | Feller et al. | |
| 2008/0109057 | A1 | 5/2008 | Calabria et al. | |
| 2008/0109063 | A1 | 5/2008 | Hancock et al. | |
| 2008/0114391 | A1 | 5/2008 | Dieck et al. | |
| 2008/0114436 | A1 | 5/2008 | Dieck et al. | |
| 2008/0114439 | A1 | 5/2008 | Ramaiah et al. | |
| 2008/0119886 | A1* | 5/2008 | Greenhalgh | A61B 17/12172 606/200 |
| 2008/0125806 | A1 | 5/2008 | Mazzocchi et al. | |
| 2008/0125848 | A1 | 5/2008 | Kusleika et al. | |
| 2008/0125852 | A1 | 5/2008 | Garrison et al. | |
| 2008/0132820 | A1 | 6/2008 | Buckman et al. | |
| 2008/0132989 | A1 | 6/2008 | Snow et al. | |
| 2008/0140177 | A1 | 6/2008 | Hines | |
| 2008/0154286 | A1 | 6/2008 | Abbott et al. | |
| 2008/0195139 | A1 | 8/2008 | Donald et al. | |
| 2008/0200945 | A1 | 8/2008 | Amplatz et al. | |
| 2008/0200979 | A1 | 8/2008 | Dieck et al. | |
| 2008/0219533 | A1 | 9/2008 | Grigorescu | |
| 2008/0221600 | A1 | 9/2008 | Dieck et al. | |
| 2008/0243226 | A1 | 10/2008 | Fernandez et al. | |
| 2008/0249562 | A1 | 10/2008 | Cahill | |
| 2008/0255603 | A1* | 10/2008 | Naor | A61F 2/00 606/200 |
| 2008/0262598 | A1 | 10/2008 | Elmaleh | |
| 2008/0281350 | A1 | 11/2008 | Sepetka et al. | |
| 2008/0319533 | A1 | 12/2008 | Lehe | |
| 2009/0018637 | A1 | 1/2009 | Paul et al. | |
| 2009/0024224 | A1 | 1/2009 | Chen et al. | |
| 2009/0025820 | A1 | 1/2009 | Adams | |
| 2009/0043375 | A1 | 2/2009 | Rudakov et al. | |
| 2009/0056722 | A1 | 3/2009 | Swann | |
| 2009/0062899 | A1 | 3/2009 | Dang et al. | |
| 2009/0069806 | A1 | 3/2009 | De La Mora et al. | |
| 2009/0076540 | A1 | 3/2009 | Marks et al. | |
| 2009/0082803 | A1 | 3/2009 | Adams et al. | |
| 2009/0099647 | A1* | 4/2009 | Glimsdale | A61B 17/12172 623/1.35 |
| 2009/0112249 | A1 | 4/2009 | Miles et al. | |
| 2009/0112251 | A1 | 4/2009 | Qian et al. | |
| 2009/0118811 | A1 | 5/2009 | Moloney | |
| 2009/0125094 | A1 | 5/2009 | Rust | |
| 2009/0125119 | A1 | 5/2009 | Obermiller et al. | |
| 2009/0143849 | A1 | 6/2009 | Ozawa et al. | |
| 2009/0143851 | A1 | 6/2009 | Paul, Jr. | |
| 2009/0148492 | A1 | 6/2009 | Dave et al. | |
| 2009/0155367 | A1 | 6/2009 | Neuwirth et al. | |
| 2009/0187214 | A1 | 7/2009 | Amplatz et al. | |
| 2009/0192587 | A1* | 7/2009 | Frid | A61F 2/90 623/1.15 |
| 2009/0198315 | A1 | 8/2009 | Boudjemline | |
| 2009/0204145 | A1 | 8/2009 | Matthews | |
| 2009/0210047 | A1 | 8/2009 | Amplatz et al. | |
| 2009/0216307 | A1 | 8/2009 | Kaufmann et al. | |
| 2009/0228029 | A1 | 9/2009 | Lee | |
| 2009/0228093 | A1 | 9/2009 | Taylor et al. | |
| 2009/0259202 | A1 | 10/2009 | Leeflang et al. | |
| 2009/0264914 | A1 | 10/2009 | Riina et al. | |
| 2009/0264978 | A1 | 10/2009 | Dieck et al. | |
| 2009/0275974 | A1 | 11/2009 | Marchand et al. | |
| 2009/0287291 | A1 | 11/2009 | Becking et al. | |
| 2009/0287292 | A1 | 11/2009 | Becking et al. | |
| 2009/0287294 | A1 | 11/2009 | Rosqueta et al. | |
| 2009/0287297 | A1 | 11/2009 | Cox | |
| 2009/0297582 | A1 | 12/2009 | Meyer et al. | |
| 2009/0306702 | A1 | 12/2009 | Miloslavski et al. | |
| 2009/0318892 | A1 | 12/2009 | Aboytes et al. | |
| 2009/0318941 | A1 | 12/2009 | Sepetka et al. | |
| 2009/0318948 | A1 | 12/2009 | Davis et al. | |
| 2009/0319023 | A1 | 12/2009 | Hildebrand et al. | |
| 2010/0004726 | A1 | 1/2010 | Hancock et al. | |
| 2010/0004761 | A1 | 1/2010 | Flanders et al. | |
| 2010/0023048 | A1 | 1/2010 | Mach | |
| 2010/0023105 | A1 | 1/2010 | Levy et al. | |
| 2010/0030200 | A1 | 2/2010 | Strauss et al. | |
| 2010/0030220 | A1 | 2/2010 | Truckai et al. | |
| 2010/0036390 | A1 | 2/2010 | Gumm | |
| 2010/0036410 | A1 | 2/2010 | Krolik et al. | |
| 2010/0042133 | A1 | 2/2010 | Ramzipoor et al. | |
| 2010/0069948 | A1 | 3/2010 | Veznedaroglu et al. | |
| 2010/0087908 | A1 | 4/2010 | Hilaire et al. | |
| 2010/0094335 | A1 | 4/2010 | Gerberding et al. | |
| 2010/0106178 | A1 | 4/2010 | Obermiller et al. | |
| 2010/0131002 | A1 | 5/2010 | Connor et al. | |
| 2010/0139465 | A1 | 6/2010 | Christian et al. | |
| 2010/0144895 | A1 | 6/2010 | Porter | |
| 2010/0152767 | A1 | 6/2010 | Greenhalgh et al. | |
| 2010/0174269 | A1 | 7/2010 | Tompkins et al. | |

(56) References Cited

U.S. PATENT DOCUMENTS

| | | | |
|---|---|---|---|
| 2010/0185271 | A1 | 7/2010 | Zhang |
| 2010/0222802 | A1 | 9/2010 | Gillespie, Jr. et al. |
| 2010/0228184 | A1 | 9/2010 | Mavani et al. |
| 2010/0249830 | A1 | 9/2010 | Nelson |
| 2010/0249894 | A1 | 9/2010 | Oba et al. |
| 2010/0256527 | A1 | 10/2010 | Lippert et al. |
| 2010/0256528 | A1 | 10/2010 | Lippert et al. |
| 2010/0256601 | A1 | 10/2010 | Lippert et al. |
| 2010/0256602 | A1 | 10/2010 | Lippert et al. |
| 2010/0256603 | A1 | 10/2010 | Lippert et al. |
| 2010/0256604 | A1 | 10/2010 | Lippert et al. |
| 2010/0256605 | A1 | 10/2010 | Lippert et al. |
| 2010/0256606 | A1 | 10/2010 | Lippert et al. |
| 2010/0262014 | A1 | 10/2010 | Huang |
| 2010/0268201 | A1 | 10/2010 | Tieu et al. |
| 2010/0268260 | A1 | 10/2010 | Riina et al. |
| 2010/0274276 | A1 | 10/2010 | Chow et al. |
| 2010/0298791 | A1 | 11/2010 | Jones et al. |
| 2010/0312061 | A1 | 12/2010 | Hess et al. |
| 2010/0312270 | A1 | 12/2010 | Mcguckin, Jr. et al. |
| 2010/0331948 | A1 | 12/2010 | Turovskiy et al. |
| 2011/0022149 | A1 | 1/2011 | Cox et al. |
| 2011/0046658 | A1 | 2/2011 | Connor et al. |
| 2011/0054519 | A1 | 3/2011 | Neuss |
| 2011/0077620 | A1 | 3/2011 | Debeer |
| 2011/0082493 | A1 | 4/2011 | Samson et al. |
| 2011/0106234 | A1 | 5/2011 | Grandt |
| 2011/0125110 | A1 | 5/2011 | Cotton |
| 2011/0137332 | A1 | 6/2011 | Sepetka et al. |
| 2011/0137405 | A1 | 6/2011 | Wilson et al. |
| 2011/0144669 | A1 | 6/2011 | Becking et al. |
| 2011/0152993 | A1 | 6/2011 | Marchand et al. |
| 2011/0166588 | A1 | 7/2011 | Connor et al. |
| 2011/0184452 | A1 | 7/2011 | Huynh et al. |
| 2011/0184453 | A1 | 7/2011 | Levy et al. |
| 2011/0196415 | A1 | 8/2011 | Ujiie et al. |
| 2011/0202085 | A1 | 8/2011 | Loganathan et al. |
| 2011/0208227 | A1 | 8/2011 | Becking |
| 2011/0224776 | A1 | 9/2011 | Sepetka et al. |
| 2011/0245862 | A1 | 10/2011 | Dieck et al. |
| 2011/0251699 | A1 | 10/2011 | Ladet |
| 2011/0265943 | A1 | 11/2011 | Rosqueta et al. |
| 2011/0276120 | A1 | 11/2011 | Gilson et al. |
| 2011/0313447 | A1 | 12/2011 | Strauss et al. |
| 2011/0319926 | A1 | 12/2011 | Becking et al. |
| 2012/0010644 | A1 | 1/2012 | Sideris et al. |
| 2012/0022572 | A1 | 1/2012 | Braun et al. |
| 2012/0041470 | A1 | 2/2012 | Shrivastava et al. |
| 2012/0041472 | A1 | 2/2012 | Tan et al. |
| 2012/0065720 | A1 | 3/2012 | Strauss et al. |
| 2012/0101510 | A1 | 4/2012 | Lenker et al. |
| 2012/0101561 | A1 | 4/2012 | Porter |
| 2012/0116350 | A1 | 5/2012 | Strauss et al. |
| 2012/0143237 | A1 | 6/2012 | Cam et al. |
| 2012/0143243 | A1 | 6/2012 | Hill et al. |
| 2012/0143317 | A1 | 6/2012 | Cam et al. |
| 2012/0165803 | A1 | 6/2012 | Bencini et al. |
| 2012/0165919 | A1 | 6/2012 | Cox et al. |
| 2012/0197283 | A1 | 8/2012 | Marchand et al. |
| 2012/0226343 | A1 | 9/2012 | Vo et al. |
| 2012/0239074 | A1 | 9/2012 | Aboytes et al. |
| 2012/0245674 | A1 | 9/2012 | Molaei et al. |
| 2012/0245675 | A1 | 9/2012 | Molaei et al. |
| 2012/0283768 | A1 | 11/2012 | Cox et al. |
| 2012/0283769 | A1 | 11/2012 | Cruise et al. |
| 2012/0310269 | A1 | 12/2012 | Fearnot et al. |
| 2012/0316598 | A1 | 12/2012 | Becking et al. |
| 2012/0316632 | A1 | 12/2012 | Gao |
| 2012/0323271 | A1 | 12/2012 | Obermiller et al. |
| 2012/0330341 | A1 | 12/2012 | Becking et al. |
| 2012/0330347 | A1 | 12/2012 | Becking et al. |
| 2012/0330348 | A1 | 12/2012 | Strauss et al. |
| 2013/0018451 | A1 | 1/2013 | Grabowski et al. |
| 2013/0066357 | A1 | 3/2013 | Aboytes et al. |
| 2013/0066360 | A1 | 3/2013 | Becking et al. |
| 2013/0085522 | A1 | 4/2013 | Becking et al. |
| 2013/0092013 | A1 | 4/2013 | Thompson et al. |
| 2013/0116722 | A1 | 5/2013 | Aboytes et al. |
| 2013/0123830 | A1 | 5/2013 | Becking et al. |
| 2013/0211495 | A1 | 8/2013 | Halden et al. |
| 2013/0233160 | A1 | 9/2013 | Marchand et al. |
| 2013/0239790 | A1 | 9/2013 | Thompson et al. |
| 2013/0245667 | A1 | 9/2013 | Marchand et al. |
| 2013/0245670 | A1 | 9/2013 | Fan |
| 2013/0268053 | A1 | 10/2013 | Molaei et al. |
| 2013/0274862 | A1 | 10/2013 | Cox et al. |
| 2013/0274863 | A1 | 10/2013 | Cox et al. |
| 2013/0274866 | A1 | 10/2013 | Cox et al. |
| 2013/0274868 | A1 | 10/2013 | Cox et al. |
| 2013/0304179 | A1 | 11/2013 | Bialas et al. |
| 2013/0345739 | A1 | 12/2013 | Brady et al. |
| 2014/0005713 | A1 | 1/2014 | Bowman |
| 2014/0012307 | A1 | 1/2014 | Franano et al. |
| 2014/0058420 | A1 | 2/2014 | Hannes et al. |
| 2014/0135810 | A1 | 5/2014 | Divino et al. |
| 2014/0135811 | A1 | 5/2014 | Divino et al. |
| 2014/0135812 | A1 | 5/2014 | Divino et al. |
| 2014/0316012 | A1 | 10/2014 | Freyman et al. |
| 2014/0371734 | A1 | 12/2014 | Truckai |
| 2015/0216684 | A1 | 8/2015 | Enzmann et al. |
| 2015/0250628 | A1 | 9/2015 | Monstadt et al. |
| 2015/0272590 | A1 | 10/2015 | Aboytes et al. |
| 2015/0313737 | A1 | 11/2015 | Tippett et al. |
| 2015/0327843 | A1 | 11/2015 | Garrison |
| 2015/0342613 | A1 | 12/2015 | Aboytes et al. |
| 2016/0022445 | A1 | 1/2016 | Ruvalcaba et al. |
| 2016/0030050 | A1 | 2/2016 | Franano et al. |
| 2016/0066921 | A1 | 3/2016 | Seifert et al. |
| 2016/0135984 | A1 | 5/2016 | Rudakov et al. |
| 2016/0206320 | A1 | 7/2016 | Connor |
| 2016/0206321 | A1 | 7/2016 | Connor |
| 2017/0150971 | A1 | 6/2017 | Hines |
| 2017/0156903 | A1 | 6/2017 | Shobayashi |
| 2017/0189035 | A1 | 7/2017 | Porter |
| 2017/0266023 | A1 | 9/2017 | Thomas |
| 2017/0340333 | A1 | 11/2017 | Badruddin et al. |
| 2017/0367708 | A1 | 12/2017 | Mayer et al. |
| 2018/0049859 | A1 | 2/2018 | Stoppenhagen et al. |
| 2018/0125686 | A1 | 5/2018 | Lu |
| 2018/0140305 | A1 | 5/2018 | Connor |
| 2018/0161185 | A1 | 6/2018 | Kresslein et al. |
| 2018/0193025 | A1 | 7/2018 | Walzman |
| 2018/0193026 | A1 | 7/2018 | Yang et al. |
| 2018/0206852 | A1 | 7/2018 | Moeller |
| 2019/0053811 | A1 | 2/2019 | Garza et al. |
| 2019/0282242 | A1 | 9/2019 | Divino et al. |
| 2019/0343532 | A1 | 11/2019 | Divino et al. |
| 2020/0061099 | A1 | 2/2020 | Li et al. |
| 2022/0022886 | A1 | 1/2022 | Becking et al. |

FOREIGN PATENT DOCUMENTS

| | | | |
|---|---|---|---|
| CN | 102083493 | A | 6/2011 |
| DE | 1283434 | B | 11/1968 |
| DE | 102008028308 | A1 | 4/2009 |
| DE | 102010050569 | A1 | 5/2012 |
| DE | 102011011510 | A1 | 8/2012 |
| DE | 102011102933 | A1 | 12/2012 |
| EP | 0717969 | A2 | 6/1996 |
| EP | 0743047 | A2 | 11/1996 |
| EP | 0855170 | A2 | 7/1998 |
| EP | 0775470 | B1 | 3/1999 |
| EP | 1188414 | A1 | 3/2002 |
| EP | 1621148 | A1 | 2/2006 |
| EP | 1637176 | A1 | 3/2006 |
| EP | 1752112 | A1 | 2/2007 |
| EP | 1813213 | A2 | 8/2007 |
| EP | 1923019 | A1 | 5/2008 |
| EP | 1942972 | A1 | 7/2008 |
| EP | 1872742 | B1 | 5/2009 |
| EP | 2208483 | A1 | 7/2010 |
| EP | 2279023 | A2 | 2/2011 |
| EP | 2363075 | A1 | 9/2011 |
| EP | 2496299 | A2 | 9/2012 |

(56) References Cited

FOREIGN PATENT DOCUMENTS

| | | | |
|---|---|---|---|
| EP | 2675402 | A2 | 12/2013 |
| FR | 2556210 | B1 | 4/1988 |
| FR | 2890306 | A1 | 3/2007 |
| JP | 11506686 | | 6/1999 |
| JP | 2003520103 | A | 7/2003 |
| JP | 2003524434 | A | 8/2003 |
| JP | 2004049585 | A | 2/2004 |
| JP | 2005522266 | A | 7/2005 |
| JP | 2005261951 | A | 9/2005 |
| JP | 2006506201 | A | 2/2006 |
| JP | 2008521492 | A | 6/2008 |
| JP | 2008541832 | A | 11/2008 |
| JP | 4673987 | B2 | 1/2011 |
| WO | WO 8800813 | A1 | 2/1988 |
| WO | 9406502 | A2 | 3/1994 |
| WO | WO 9601591 | A1 | 1/1996 |
| WO | WO 9726939 | A1 | 7/1997 |
| WO | WO 9903404 | A1 | 1/1999 |
| WO | WO 9905977 | A1 | 2/1999 |
| WO | WO 9908607 | A1 | 2/1999 |
| WO | WO 9908743 | A1 | 2/1999 |
| WO | WO 9940873 | A1 | 8/1999 |
| WO | WO 9962432 | A1 | 12/1999 |
| WO | WO 0057815 | A1 | 10/2000 |
| WO | WO 0193782 | A1 | 12/2001 |
| WO | WO 0200139 | A1 | 1/2002 |
| WO | WO 02071977 | A2 | 9/2002 |
| WO | 03011151 | A1 | 2/2003 |
| WO | WO 03037191 | A1 | 5/2003 |
| WO | WO 2005117718 | A1 | 12/2005 |
| WO | 2006034149 | A2 | 3/2006 |
| WO | WO 2006026744 | A1 | 3/2006 |
| WO | WO 2006034166 | A2 | 3/2006 |
| WO | WO 2006052322 | A2 | 5/2006 |
| WO | WO 2006091891 | A2 | 8/2006 |
| WO | WO 2006119422 | A2 | 11/2006 |
| WO | 2007006139 | A1 | 1/2007 |
| WO | WO 2007047851 | A2 | 4/2007 |
| WO | WO 2007076480 | A2 | 7/2007 |
| WO | WO 2007095031 | A2 | 8/2007 |
| WO | WO 2007121405 | A2 | 10/2007 |
| WO | WO 2008022327 | A2 | 2/2008 |
| WO | 2008074027 | A1 | 6/2008 |
| WO | WO 2008109228 | A2 | 9/2008 |
| WO | WO 2008151204 | A1 | 12/2008 |
| WO | WO 2008157507 | A2 | 12/2008 |
| WO | 2009014528 | A1 | 1/2009 |
| WO | WO 2009076515 | A1 | 6/2009 |
| WO | WO 2009132045 | A2 | 10/2009 |
| WO | WO 2009134337 | A1 | 11/2009 |
| WO | WO 2009135166 | A2 | 11/2009 |
| WO | 2010009019 | A1 | 1/2010 |
| WO | 2010027363 | A1 | 3/2010 |
| WO | 2010028300 | A1 | 3/2010 |
| WO | WO 2010030991 | A1 | 3/2010 |
| WO | 2010077599 | A1 | 7/2010 |
| WO | WO 2010147808 | A1 | 12/2010 |
| WO | WO 2011057002 | A2 | 5/2011 |
| WO | WO 2011057277 | A2 | 5/2011 |
| WO | WO 2011066962 | A1 | 6/2011 |
| WO | 2011095966 | A1 | 8/2011 |
| WO | WO 2011130081 | A1 | 10/2011 |
| WO | WO 2011153304 | A1 | 12/2011 |
| WO | 2012034135 | A1 | 3/2012 |
| WO | WO 2012068175 | A2 | 5/2012 |
| WO | WO 2012112749 | A2 | 8/2012 |
| WO | WO 2012166804 | A1 | 12/2012 |
| WO | 2013112944 | A1 | 8/2013 |
| WO | 2013138615 | A2 | 9/2013 |
| WO | 2013138615 | A3 | 9/2014 |
| WO | WO 2017074411 | A1 | 5/2017 |
| WO | WO 2018051187 | A1 | 3/2018 |

OTHER PUBLICATIONS

Thorell, et al., "Y-configured Dual Intracranial Stent-assisted Coil Embolization for the Treatment of Wide-necked Basilar Tip Aneurysms", Neurosurgery, May 2005, vol. 56, Issue 5, pp. 1035-1040.

Hill , et al., "Initial Results of the AMPLATZER Vascular Plug in the Treatment of Congenital Heart Disease, Business Briefing", US Cardiology 2004.

* cited by examiner

MULTIPLE LAYER FILAMENTARY DEVICES FOR TREATMENT OF VASCULAR DEFECTS

CROSS-REFERENCE TO RELATED APPLICATION(S)

The present application is a continuation of U.S. patent application Ser. No. 15/415,669, filed Jan. 25, 2017, which is a continuation of U.S. patent application Ser. No. 13/470,013, filed May 11, 2012, now U.S. Pat. No. 9,585,669, which is a continuation of U.S. patent application Ser. No. 12/911,034, filed Oct. 25, 2010, now U.S. Pat. No. 9,039,726, which is a continuation of U.S. patent application Ser. No. 12/427,620, filed Apr. 21, 2009, now U.S. Pat. No. 8,142,456, which claims the benefit of each of: U.S. Patent Application Ser. No. 61/046,594 and 61/046,670, both filed Apr. 21, 2008; U.S. Patent Application Ser. No. 61/083,957 and 61/083,961, both filed Jul. 28, 2008; and U.S. Patent Application Ser. No. 61/145,097, filed Jan. 15, 2009. Each of the foregoing applications is incorporated herein by reference in its entirety.

TECHNICAL FIELD

The present invention is directed to braid-balls suitable for aneurysm occlusion and/or parent vessel occlusion/sacrifice (e.g., in treating neurovascular defects).

BACKGROUND

Mainstream clinical practice in endovascular treatment of intracranial aneurysms has changed little since the 1990's when vasoocclusive coil use became widespread. Certainly, improved catheters and other auxiliary devices (e.g., stents) have helped make coiling procedures safer and/or more effective. However, the art in achieving adequate and appropriate aneurysm coil packing is best accomplished by the most highly skilled physicians.

Where practicable, aneurysm exclusion by cover-type devices (e.g., as described in U.S. patent application Ser. No. 12/397,123 to the assignee hereof) may be preferred. Certain other groups are attempting to shift the paradigm away from intra-aneurysm coil packing to achieve embolization via deployment of an extra-aneurysm flow disruptor/diverter stent in the parent vessel. These densely braided devices and/or multiple braid devices layered upon one another are placed in the parent vessel across the neck of an aneurysm with the intent to alter hemodynamics so as to effect embolization.

These WALLSTENT-like devices are best suited for placement across sidewall aneurysms. Yet, terminal aneurysms (e.g., bifurcation aneurysms) are estimated by some to make-up between about 60 and 80% of all aneurysm occurrences. By most optimistic count, only about 40% of intracranial aneurysms can be treated using the referenced stent-like devices.

Numerous other devices have been conceived in effort to address terminal aneurysms. Complicated and/or impracticable deployment is common to many. Others simply serve as adjunctive to coils or liquid embolic agents. In these latter examples, procedures may become even more complicated and require even greater physician skill than a standard coiling procedure.

A simpler, yet promising solution is proposed in PCT/US 2007/0076232 to Dieck, et al. A braided/mesh conical member is described for diverting blood flow from the aneurysm neck. A base of the device is set inside the aneurysm while a flow diverter portion extends into the parent vessel to direct blood flow toward adjacent side branches and away from the aneurysm. The implant may be positioned within the aneurysm as a stand-alone device or be supported by a connected stent-like body.

U.S. Pat. Nos. 6,168,622 and 6,506,204 to Mazzochi, et al. disclose another type of braided flow disruptor set at least partly within an aneurysm. A bulbous portion is adapted to fit within the aneurysm dome and is anchored on the outside by a neck-covering flap. Given the manner in which bifurcation aneurysms often incorporate branch vessel anatomy, such a patch would often interfere with and/or "flap" free raising significant issues of potentially pathological thrombus formation within the parent vessel.

SUMMARY OF THE INVENTION

Implants of the present invention address shortcomings of each of the above-referenced devices. As such, the subject implants (as well as their associated delivery systems) offer potential to advance the state of the art in endovascular treatment of vascular malformations, including aneurysms.

The present invention is directed to wire braid ball implants for occluding blood flow at endovascular sites. Delivery systems and methods of making the balls are also described. The balls are useful for treating neurovascular defects. One use is in intracranial aneurysm embolization/occlusion and another in parent vessel occlusion (PVO) or sacrifice.

Generally speaking, the subject vascular implants are braided devices using a combination of bio-stable materials selected from Stainless Steel, Cobalt Chromium, Nitinol, Titanium, Titanium-alloys, Zirconium and Zirconium alloys, PET (or another suture material) and medical-grade adhesive. The density of the device is paramount in applications where the braid itself is intended to affect blood flow, allowing thrombosis within a volume formed by the ball to occlude a site. As such, high density braid/mesh is typically required. Namely, braid having at least about 48 ends, typically set at about 90 degrees or greater, in diameters from about 4 to about 8 mm may be employed. At larger diameters (e.g., about 6 mm to 12 mm or more), more wire ends (e.g., common multiples of 64, 72, 96, 128, 144) may be employed in forming the balls. Still higher typical wire counts may be employed. Either one of commercially available 192 and 288 carrier standard braiders may be employed. Moreover, 3-D braiding technology (such services are provided by 3Tex, Inc.) may be employed in forming the braid matrix from which the balls are formed. In addition, any combination of wire diameter, wire count, braid angle, and per-inch crossings can be used to make braid in order to configure an embolic and blood flow occlusive device deemed appropriate for a particular vascular site.

A range of wire sizes or combination of wire sizes may be employed, typically ranging from about 0.0008 to about 0.0015 inch, and up to about 0.003 inches depending on desired delivery profile (which is typically desired to be less than about 0.050 inches—at least for neurovascular indications—and more generally up to about 0.070 for peripheral PVO indications). A single braid tube may have all wires the same diameter, or may have some wires of a slightly thicker diameter to impart additional strength to the braid layer. For example, half the wires of a 96 wire tube (i.e., 48 ends) can be e.g. 0.001" diameter and the other half of the wires can be e.g. 0.0015" diameter. In which case, the two wire sizes would typically be interlaced uniformly in making the braid.

The thicker wires impart greater strength to the braid without significantly increasing the device delivery profile, with the thinner wires offering some strength while filling out the braid matrix density.

The wire is preferably NiTi alloy that is superelastic at body temperature. The metal may be a binary alloy or a ternary alloy to provide additional radiopacity. Alternatively, radiopaque platinum fibers may be included in the braid, or the wire may comprise platinum or gold core Nitinol DFT. Otherwise, hubs, bands or wraps (preferably Pt) used to secure the braid wire (at either or both distal and proximal ends, and also in between caps where appropriate) may serve as the sole radiopaque feature(s).

To improve implant wire corrosion resistance and/or biocompatibility after heat setting shape, the implants may be etched in "AYA" Sulfamic Acid solution, then passivated in Nitric acid solution. Alternatively or additionally, pre-etched and/or polished wire may be employed in braiding the implant matrix. Shape setting the braid in the implant shape may be performed in an oven/furnace, a fluidized bath or salt pot. All such processing is within ken of those with ordinary skill in the art.

Especially after heatsetting the shape, the wire may be coated with an agent for promoting a desired biological effect. For example, wire can be coated with a thrombogenic or an endothelization agent, or other agent capable of promoting a desired biological process at the target site. The braid balls may also be partially or fully coated on the exterior (e.g., with coating such as urethane) to increase the occlusive effect of the ball, provided the coating does not cause the delivery profile of the final device to exceed allowed limits. Hydrogel coating also offers an appealing option, such as a hydrogel-based polymer network capable of entrapping therapeutic agents as described in U.S. Pat. No. 6,905,700 to Won et al.

Likewise, while the balls advantageously comprise Nitinol braid, the braid may instead comprise polymer—especially high strength biodegradable polymer such as MX-2 (MAX-Prene), synthetic absorbable monofilament (90/10 Glycolide/L-Lactide) and/or G-2 (Glycoprene), synthetic absorbable monofilament (Glycolide (PGA), ε-Caprolactone (PCL), Trimethylene Carbonate (TMC) Copolymer) that is heat set into shape (e.g., at 110 degrees centigrade for an hour).

Deliverability of the subject implants to certain neurovascular sites (e.g., distal intercranial aneurysms) often requires that they be compressible to pass through a catheter sized for navigating the narrow and tortuous vessels of the brain. Standard neurovascular catheters suitable for such use have 0.021" and 0.027" lumen diameters. Especially for higher wire count balls 0.027" ID (e.g., Cordis Mass Transit Boston Scientific Renegade HI-FLO) or larger (e.g., 0.044" ID Concentric Merci Distal Access Catheter) commercially available micro catheters may be preferred. For devices adapted to address PVO indications in which higher wire counts and/or larger wire diameters are used to ensure anchoring, the implants may require 5 and/or 6 Fr guide catheters for delivery.

In any of the configurations described, the devices may comprise high-density Nitinol braid that is folded/doubled-back upon itself and heatset to provide an open body having two adjacent layers forming an even denser matrix to occlude blood flow. The folded-back (inverted or everted) section may be closed to define a distal end of the device where a radiopaque feature may be located. At the opposite side of the implant, braid filaments are held in a hub including at least an outer band.

A port within the hub can receive component(s) of an optional detachable pusher. Alternatively, the implant can be deployed through a catheter using a simple pusher. Braid filaments within the hub(s) may be welded to each other and/or the band. Alternatively, the braid and hub(s) may be secured using biocompatible adhesive.

In a relaxed state, the implants define an open, preferably rounded, volume. In a delivery catheter, they compress into a substantially cylindrical body. When deployed at a treatment site, they expand to abut surrounding tissue and occlude flow in a clinically relevant timeframe.

Use of a detachable pusher allows for deploying a device (e.g., in an aneurysm) and checking fit. Deployed in an aneurysm to occlude the aneurysm at its neck, the implant device largely assumes the shape of the aneurysm, with the proximal hub and closely adjacent braid material outside the neck. To achieve such fit, the implants are provided in a range of sizes. These may progress in 0.5 mm to 1 mm diameter increments. For aneurysm treatment at bifurcations, it may also be desirable if the ball (at least in its delivered configuration) assumes a tear-drop shape to assist in a flow-divider/diverter type function as described in Dieck, et al., referenced above.

Should the selected implant not fit as desired, however, it can simply be withdrawn back into the delivery catheter. If desired fit is achieved (with the first implant or a replacement) as confirmed by medical imaging, the implant is released.

An electrolytically-releasable GDC-type joint can be used hold the implant secure to the pusher until release. Details regarding suitable electrolytic detachment systems can be appreciated and applied to the current system as taught in U.S. Pat. No. 5,122,136 to Guglielmi and continuing applications thereof—all of which are herein incorporated by reference. Another electrically-powered detachment approach employs a meltable fiber or suture junction connecting the implant to the delivery pusher/guide. In such a system, a polymeric core may be configured with helically wound conducting ribbons held to the core. Upon application of voltage, sufficient current is conveyed through the ribbons to a wire bridge connecting them. Heat generated along the bridge, optionally NiChrome wire, severs the suture that is tied onto or running adjacent to the bridge in order to release the implant. Further details of a suitable suture-melt detachment systems are described in the incorporated provisional applications.

Yet, mechanical detachment systems may be more preferred. An aspect of the present invention involves pushers in which at least one member provides mechanical interference at/with the implant hub port to releasably lock the implant onto the pusher. In one approach, a wire or ribbon exiting an extension of the pusher threaded through the port produces such interference until it is withdrawn. In another example, a plurality of wires/ribbons are received through the port. One or more (typically two or three) of these wires extend through a pusher catheter body to a proximal handle interface. A final "anchor" wire received through the port may also extend to the handle. The anchor wire includes a head sized to exit the hub port only after the other "control" wires are cleared therefrom. The head is preferably formed by laser or plasma heating/melting. The handle provides a user interface to first remove the control wires, and then (optionally) also pull the final anchor wire.

To assist in implant recapture should it not be released, a smooth lead-in/trumpet shaped recapture profile may be provided between the hub and main body of the implant. In another approach relevant in a two-layer implant, no such profile is provided. Rather only the outer of braid layer is secured within the hub, and the inner layer "floats". In this way, only the outer layer must be straightened relative to the hub to retrieve the ball within the catheter/sheath, with the inner layer riding along.

In order to permit such action, the braid matrix must remain stable and interlocked. Accordingly, when feasible, a one-over-one braid pattern will be preferred. In addition, the braid should be trimmed adjacent the hub where the hub-secured braid is most dense. So configured, the outer braid both serves as a guide and is of such density to prevent loose ends of the inner layer from poking through. Whereas a floating-layer type ball implant would typically only be used for an aneurysm indication due to reduced radial strength, the recapture profile may be used on either an implant intended for aneurysm or PVO use.

Recapture features aside, when deployed in a vessel for use in parent vessel occlusion, the subject implant is "sausage" shaped. For such purposes, it may be desirable that the compressed length of the ball is minimized relative to its diameter. Proximal and/or distal ends of the ball may be flattened or flatter (such that the ball is more "donut" shaped) for this purpose.

Oversizing the device relative to the vessel provides adequate radial force to anchor its position against blood flow/pressure. To generate more anchoring force within a vessel for a PVO-dedicated implant (i.e., of a given deployed length), the ball may be formed in a shape having an elliptical cross-section. To offer further improved vessel anchoring, a cylindrical waist may be incorporated in the shape. Edges formed will concentrate stresses on the vessel wall in some cases to improve anchoring. Yet, the bulk shape allows the implant to work within a wide range of vessel sizes. Indeed, one size may fit a wide range of vessel diameters (e.g., a 10 mm ball suitable for 3-5 mm vessels, etc.).

In either type of implant (i.e., aneurysm or PVO), an advantageous construction involves folding or doubling-back the braid during manufacture to produce a two-layer matrix. A medial crease or fold in the braid is formed that is used in defining one end of the implant.

The fold may be pre-set in the braid or formed when fixturing the braid for shape setting. In the former case, the bend is pre-set by heatsetting the braid when confined in a tight tubular shape (e.g., by a crimper or at least partially within a hypotube). In the latter case, the braid is tied with suture at a point, a form is inserted in the open end of the braid tube and the braid is stretched, or positioned, over the form with the folded section under compression. When heated to set the shape, the suture burns away as the compression force sets the fold at a minimal radius.

The fold itself proves useful in a number of ways. In one variation of the invention, the folded section provides an atraumatic end to the implant. The folded section can be left open, or tied closed by a suture, wire (or other material) loop. If not radiopaque itself, the tie may also hold a marker band (knotted, glued or crimped on). If such a marker is provided, it may advantageously be suspended adjacent the top/distal end of the ball within the interior volume.

Either way, upon compression to a delivery profile, the implant body basically pivots (rather than bends) at the fold, thus minimizing in-catheter/sheath forces. This improves device trackability as well as delivery and the ability to recapture if treatment with another size device is desirable.

In a PVO-specific implant, a marker band can be held between braid layers adjacent the medial fold. The band is securely captured and "hidden" without presenting edges or other features. As such, the distal end of the device offers a smooth delivery/tracking profile without need to otherwise secure the band.

Utilized in any such fashion (i.e., open, tied or banded), joints and other delivery profile-increasing features are avoided at one end of the ball. As such, the fold offers constructional advantages (including improved manufacturability)—as well as reducing areas for failure where ends of the braid would otherwise need to be secured. Moreover, the doubled-over tubular stock achieves excellent density while ensuring consistent compression and shape-recovery performance since the layers are well matched. So-matched, they extend/foreshorten to substantially an equal degree when exiting and (re)entering the catheter.

One variation of the invention takes advantage of the matched braid layers, and simply eliminates the fold by grinding or otherwise cutting it away after heatsetting (and, optimally, braid hub securement). So-prepared, the implant becomes more radially compliant as may be desirable for aneurysm treatment. And without any additional space taken-up by the bend in the filaments, the ball can be further compressed for delivery through the smallest microcatheters (for a given braid density) to achieve access to more distal treatment sites.

Another variation of the invention may or may not be constructed using a folded-over approach. To achieve higher braid densities without stacking up additional layers having to fit within the microcatheter lumen, additional "cap" structures can be instead incorporated in the implant. For delivery, these features neck-down or compress in series. Yet, upon exit from the microcatheter, they recover to a position adjacent the main body of the implant.

The ball body and cap portions of the implant are typically constructed from a continuous section of braid. Intermediate marker sections may be provided between the elements. A hub including a delivery system port is provided at the proximal end of the device.

The proximal caps of braid provide additional braid layers to the device at an end where occlusion of blood flow is critical. The proximal end of a ball placed in an aneurysm contacts the opening and neck of the aneurysm. To achieve greater flow occlusion, the braid caps can be single or double layer braid. One or more braid caps can be placed at the proximal end of the ball (i.e., a braid ball can have up to three braid caps, and more if feasible).

The braid caps do not function, and are not adapted to function, as anchors for the device. An anchor holds fast or checks motion of an object attached to it. To anchor something is to fix or fasten, or affix firmly an object. The balls implants are not anchored in the aneurysm or parent vessel using the braid caps. Rather, the braid caps are designed to either be adjacent the ball within an aneurysm or to fill only the neck region. In either case, the caps do not substantially engage vascular tissue adjacent the ball. They serve as occlusive elements that enhance the ball's embolic potential.

As alluded to, two types of capped braid ball implants are provided. Caps adapted to fit only in the aneurysm neck are typically round (though they may be oval) and may be offered in a variety of sizes to fit different neck sizes just as the ball portion of the implant is offered in different sizes. In other words, across a whole line of implants, each of the cap size and ball size parameters may be varied.

The caps adapted to fit in an aneurysm adjacent the ball portion of the implant are larger and shaped to conform to the ball-shaped body. Their delivery requires either compressing the ball portion of the implant within the aneurysm and deploying the cap therein, or deploying the cap outside the aneurysm and pushing it into the aneurysm in a deployed state.

Delivery of the devices with the neck-filling cap(s) or disk(s) is performed substantially the same as braid balls without such feature(s) with the exception that the delivery catheter is withdrawn further to expose the cap(s) or the catheter is stationed outside the aneurysm neck (vs. at the neck) and the implant extruded therefrom. Of course, some combination of such activity may alternatively be employed.

In any case, if the desired fit is achieved, the implant is released. Otherwise, the implant is pulled into the delivery catheter from the proximal hub. The one or more caps compress to the linear profile of the delivery/retrieval sheath, followed by the ball portion.

In yet another variation of the invention, a braid-ball is used in conjunction with a stent. The ball may be attached to a stent, with them delivered together. Alternatively, a frame or cage may be provided at the end of a stent into which the braid-ball is delivered after the stent is in place. In either case, the ball and/or frame may be sized to fill substantially all of an aneurysm or only fill the neck. Either way, the stent will serve as an anchor to prevent the ball from migrating. The frame-plus-ball solution offers certain advantages in terms of staged deliverability, whereas the ball-topped stent offers a one-shot solution achievable in a single delivery. In each example, the stent may be either self-expanding (e.g., comprising superelastic Nitinol) or balloon-expandable (e.g., comprising stainless steel and mounted on a PTCA-type balloon). Regardless, the braid-ball implant employed may be any one of those described in the present filing or those cross-referenced above.

The present invention includes the subject devices, kits in which they are included, methods of use and manufacture. A number of aspects of such manufacture are discussed above. More detailed discussion is presented in connection with the figures below.

BRIEF DESCRIPTION OF THE FIGURES

The figures provided herein are not necessarily drawn to scale, with some components and features are exaggerated for clarity. Of these.

Variations of the invention from the embodiments pictured are contemplated. Accordingly, depiction of aspects and elements of the invention in the figures is not intended to limit the scope of the invention.

DETAILED DESCRIPTION

Various exemplary embodiments of the invention are described below. Reference is made to these examples in a non-limiting sense. They are provided to illustrate more broadly applicable aspects of the present invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. All such modifications are intended to be within the scope of the claims made herein.

Figure 1A:
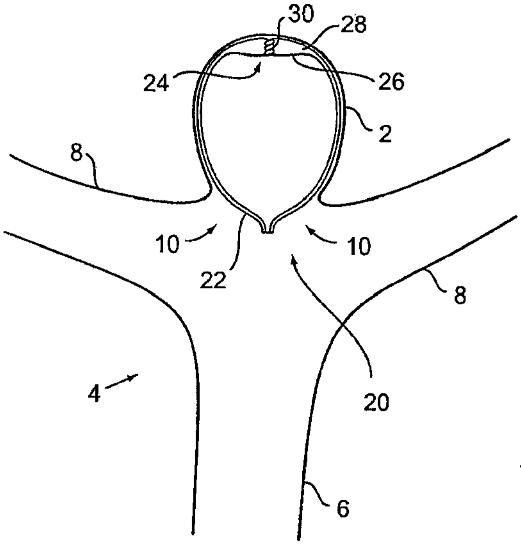
FIGS. 1A and 1B are side-sectional views illustrating braid ball implant variations in bifurcation and side-wall aneurysm locations, respectively, in which a folded section in each implant provides an atraumatic tissue interface.

Turning to FIG. 1A, it shows a first implant 20 according to the present invention. It is formed from tubular braid stock comprising a resilient material such as Nitinol, that defines an open volume (generally round, spherical, ovular, heart-shaped, etc.) in an uncompressed/constrained state.

Implant 20 is set within an aneurysm sac 2 at a vascular bifurcation 4. It is delivered by access through the trunk vessel 6 (e.g., the basilar artery), preferably through a commercially available microcatheter (not shown) with a delivery system as detailed below.

The size of the implant may be selected to fill and extend somewhat out the neck 10 of the aneurysm so the proximal end 22 of the device helps direct blood flow along the surface of the braid from which it is constructed to the branch vessels 8. A distal end of the ball is dome-shaped adjacent a fold 24 in the braid resulting in a two-layer 26, 28 (inner and outer layer, respectively) construction at least where impacted by flow at the neck 10 of the aneurysm. As shown, one or more turns of a coil 30 (e.g., Pt wire) or a band (not shown) may provide a distal radiopaque feature to mark the location of the implant.

Figure 1B:
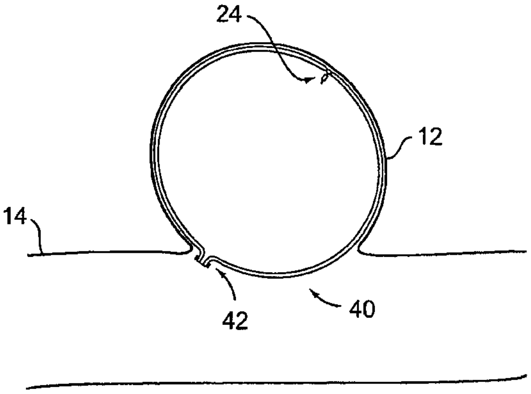

The fold 24 in the braid is set at a tighter radius in the implant 40 shown in FIG. 1B. Here, implant 40 is received within a sidewall aneurysm 12 off of a vessel 14. A hub 42 of the implant is facing blood from and directed along the line of vascular access and delivery.

Figure 2:
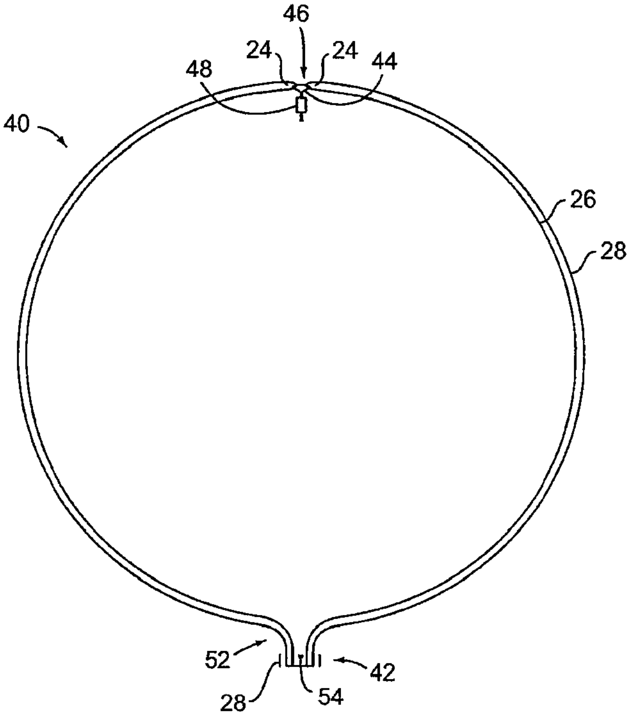
FIG. 2 is a blow-up view of the implant pictured in FIG. 1B.

As more easily seen in FIG. 2, implant 40 includes a tie 44 closing an aperture 46 defined by the fold. A radiopaque (e.g., Pt) marker 48 is held by the tie. Such a marker does not interfere with compression of the implant for delivery. Radiographic visibility of the proximal end of the ball may be achieved by virtue of the density of the braid coming together, alone, or a radiopaque (e.g., Pt) band 50 may be added.

Tie 44 may comprise any biocompatible material including Stainless Steel, Titanium, Nitinol (possibly wire that is martensitic at body temperature—commonly referred to as "muscle wire"), suture, etc. An advantage of utilizing wire is that it may simply be twisted to secure its position, along with the marker. In any case, the tie filament should be thin (e.g., about 0.0015 inch diameter or less) if a minimum-radius fold is desired.

Another salient feature of implant 40 concerns the region adjacent hub 42. Specifically, a flared or trumpet-shaped recapture profile 52 is set in the braid to aid in device recapture into the delivery catheter through which the device is advanced. An access port 54 is provided within the hub. This port accepts a delivery system interface. Delivery system construction as well as further optional details of the implant are provided below.

Of course, FIG. 2 shows a ball in an unconstrained condition. When set within an aneurysm, the implant will instead substantially conform to its shape (e.g., as shown in FIG. 1A). Generally, the implant will be oversized somewhat to exert some small load on the aneurysm wall to help maintain a stable position of the ball. However, the ball may be intentionally undersized, especially in a side-wall application (e.g., as shown in FIG. 1B) should it be desired that any hub feature is able to turn with the ball to trail with the blood flow.

Figure 3A:
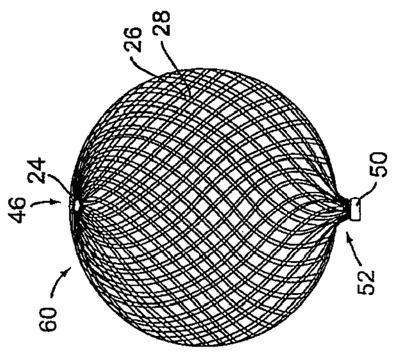
FIGS. 3A-3C are perspective side views of a folded-section braid ball in progressively larger sizes.
Figure 3B:
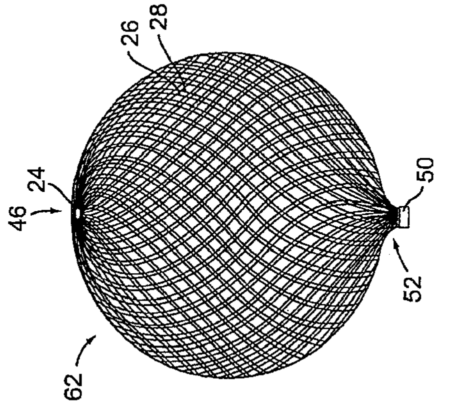
Figure 3C:
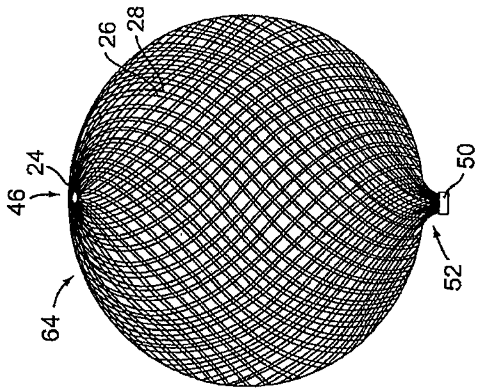

Depending on the desired fit, the implant selected by the physician may turn out to be not exactly the right size upon delivery due to variability of aneurysm morphology and/or limitations of medical imaging. It is then that the recapture profile is most useful by facilitating implant retrieval. The first implant can be discarded in favor of a second with a more appropriate size. FIGS. 3A-3C illustrate implants 60, 62 and 64 in a gradation of sizes. Naturally, the sizing interval may be varied. Likewise, the shape may be varied.

In the three examples provided, it is notable that a consistent pore size is maintained toward the center of the ball. Generally it will be desirable to minimize overall pore size. However, the density of the braid that can be achieved in braiding a given tube of braid stock is limited by its diameter and wire size. Accordingly, each of the three balls shown is made of braid incorporating a different number of wires or "ends". For example, the first implant 60 may be produced from folded-over 72-end material braided over a 6 mm diameter mandrel, the second implant 62 made of folded over 96-end braid from an 8 mm mandrel, and the third implant 64 made of folded-over 144-end braid made on a 10 mm mandrel. Alternately, the larger implants (i.e., those around 10 mm in diameter) may also be made of 96-end braid in order to maintain a lower crossing profile. Specifically, 0.027 inch catheter crossing profile can be achieved when using 96-end braid made of 0.001" diameter wire. Likewise, at the smaller end of the range (e.g., around 5 mm in diameter) 64-end braid may instead be selected to achieve 0.021 inch crossing profiles.

In any case, braid filaments are shown in pairs within these implants—one from each layer 26, 28. While the organization of the braid is often more random, the double/dual layer construction—on average—results in higher density than might be achieved with a single-layer implant due to limitations on braid density for a given starting diameter of braid.

Figure 4A:
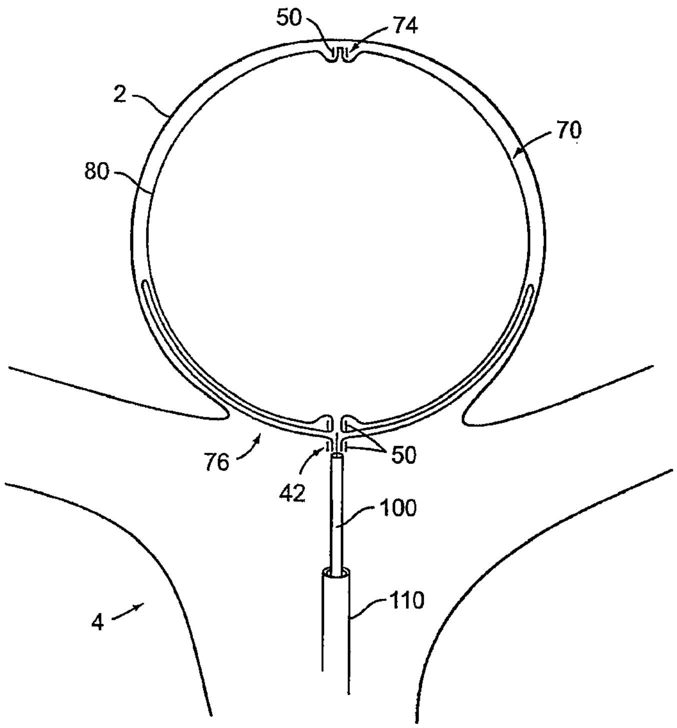
FIGS. 4A and 4B are side-sectional views illustrating proximal-flap braid ball implant variations deployed within bifurcation aneurysm locations.
Figure 4B:
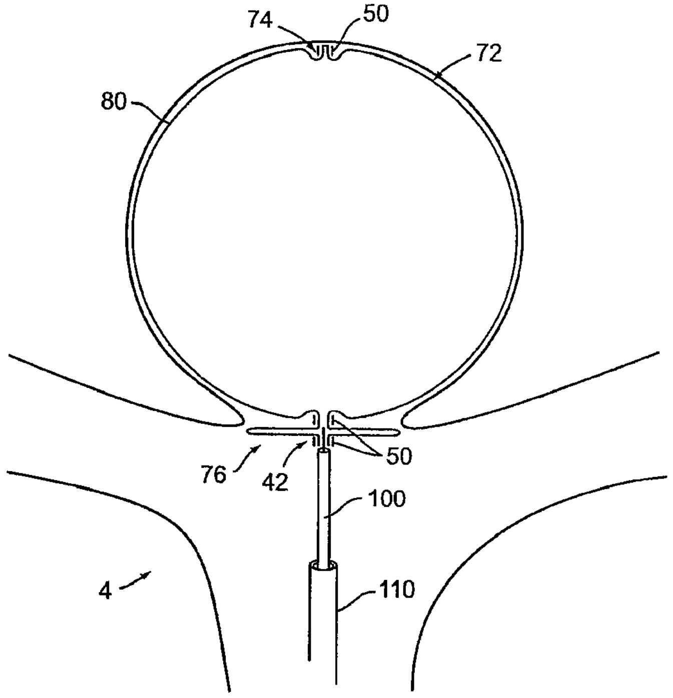

The implants 70, 72 shown in FIGS. 4A and 4B, respectively, may also be dual layer construction. In which case, they would share their distal configuration with the previous implants 20/40/60. As shown, they are single-layer devices in which the distal end takes the form of an inset hub 74.

Either way, the implants include unique proximal-end configurations. In addition to a ball or bulbous portion 80, each implant includes a flap 76 intended to improve its blood flow disruption potential. Flap 76 included in implant 70 is intended for intra-aneurysmal use. To deliver it as shown, the ball or bulbous portion is first delivered into the aneurysm sac 2. Then, that portion of the device is compressed while still mounted to pusher 100 to deploy the flap section therein. After final positioning is achieved as shown in FIG. 4A, then the pusher locking member(s) received within hub 42 are released. Finally, the pusher is withdrawn into the delivery catheter 110. To assist in the delivery method, one or more additional radiopaque features (such as a band 50 at the proximal end of ball section 80) may be provided so that deployment can be visualized at each stage.

The implant in FIG. 4B requires no such complication in delivery. Because flap 76 is of a size selected only to fill the aneurysm neck, it can be delivered straight-away. Still, intermediate radiopaque features may be desirable to confirm appropriate fit and/or deployment.

As pictured, the ball-and-disk variation of the implant shown in FIG. 4B may only be applicable to smaller-neck aneurysms as compared to the FIG. 4A "acorn" type variation. Generally, the size of the disc will not be significantly larger than the parent/trunk vessel 6 diameter and/or that of the bifurcation region 4. Otherwise, the vasculature will interfere with deployment. As such, the disk may be limited to about 2.5 to about 5 mm in diameter.

While understood better in the context of the implant manufacture steps below, flap 76 may be formed using a simple washer or plate over which the braid is heat set. Otherwise, the forming tool may be curved or dished so that flap 76 better follows the contour of the main implant body.

Flap 76 in the FIG. 4A variation will typically be formed using a concave/convex form in similar fashion. The size of this flap may vary. As shown, its outer extent is roughly the same diameter of the ball portion 80 of the device. It may be smaller and/or cover a lesser extent of the proximal side of implant 70. Generally, flap 76 will cover at least about a third and as much as one-half of body 80. In this way, adequate neck coverage is better insured when employed to treat wide-neck aneurysms.

Figure 5A:
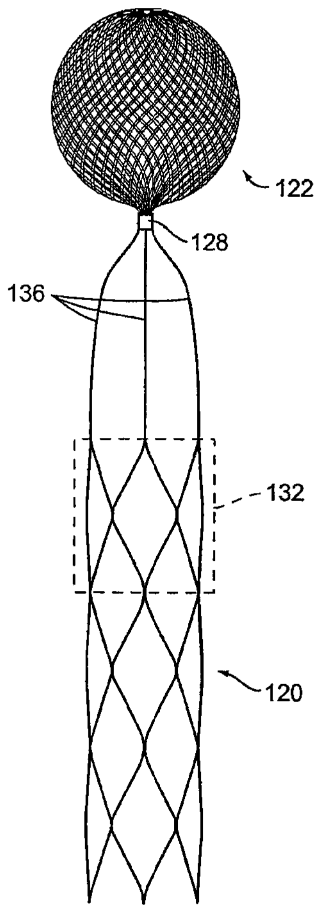
FIG. 5A is a side view of a stent-anchored version of a braid ball implant.
Figure 5B:
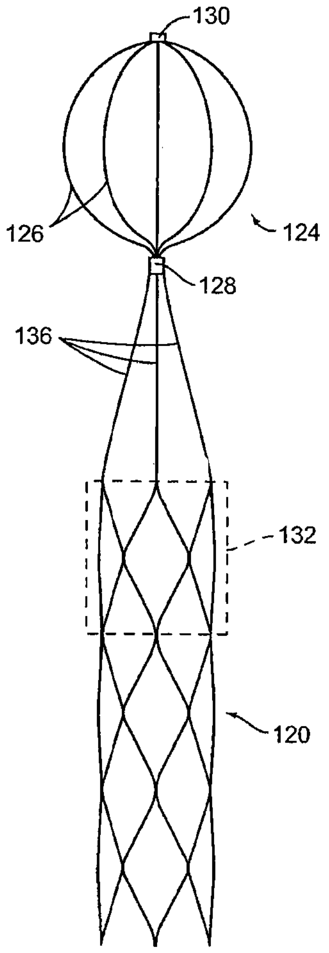
FIG. 5B is a side view a stent with a cage for receipt of a braid ball implant.

FIG. 5A is a side view of a stent-anchored version of a braid ball implant. Stent 120 is sized to anchor in the trunk vessel in treating a terminal aneurysm. This way, the ball portion 122 may be sized only to fill the neck of the aneurysm instead of its entire volume. Such an approach may be especially useful for less regularly shaped aneurysms. The device in FIG. 5B is used in a similar fashion, except that a braid-ball implant is introduced and held by a frame or cage 124, after the stent section is set in place.

The frame may comprise a plurality of individual wires 126 secured to a hub 128 of the stent at a proximal end and another hub or platten 130 at the distal end. In another variation, the wires making up the frame are cut from the same tube as the stent cells and any included hub. They may terminate at a distal end within a hub, be swaged within a radiopaque band, welded together, secured by adhesive, or attached by some other means. In any case, they are typically (though not necessarily) attached to form a closed frame. Still, an open frame is contemplated—especially one in which the wires hook backwards (i.e., proximally) to help "catch" the ball when emplaced.

These devices (i.e., those illustrated in FIGS. 5A and 5B) are delivered employing standard techniques, except that "anti-jump"/retrieval features may be incorporated into the stent section. Regardless, at least one row of stent cells 132 is provided in the stent to provide a minimum level of anchoring; however, as many as five or more may be employed—with or without any special delivery anti-jump/control features.

While the stents advantageously include three support extensions 136 for the ball or ball cage, more or fewer may be employed. However, the use of three offers the minimal stable structure available. And where they come together, they operate much like a universal joint to help end-mounted ball/frame successfully interface with the aneurysm to be treated.

Figure 6:
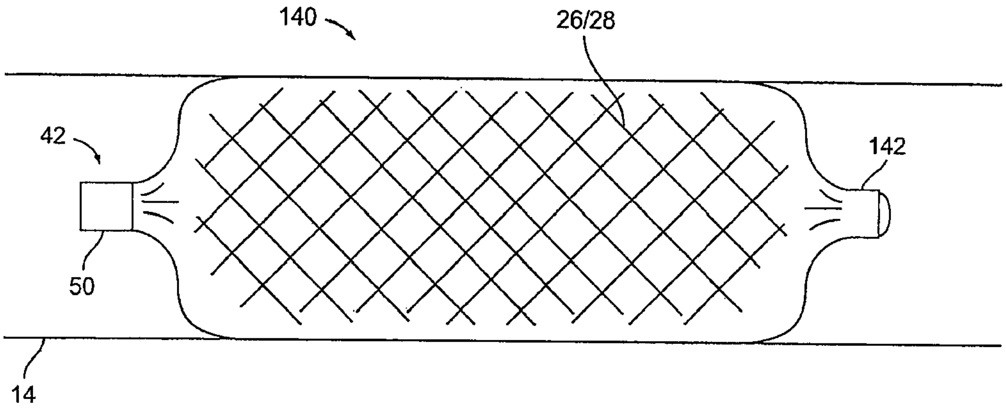
FIG. 6 is a side view illustrating a folded-section braid ball implant in a PVO application.
Figure 7:
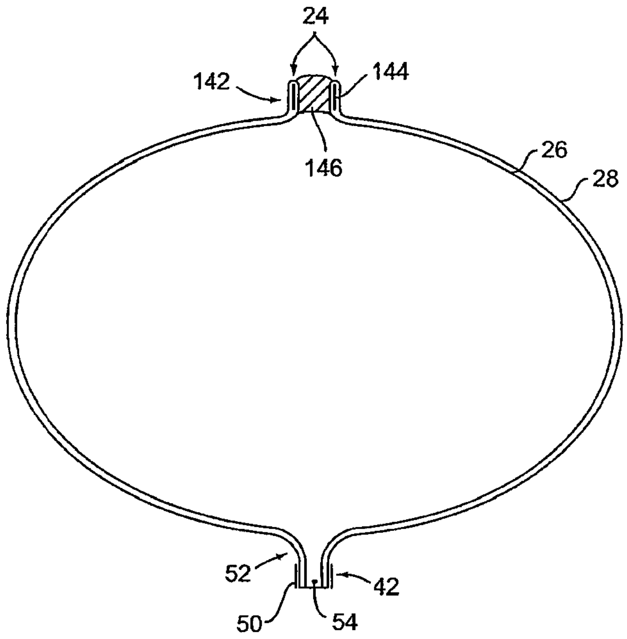
FIG. 7 is a side-sectional view of the implant in FIG. 6.

FIG. 6 illustrates an altogether different use of the subject implants. Namely, an implant 140 is deployed in a vessel (vs. adjacent a vessel within an aneurysm) to occlude flow. As referenced above, for PVO use the distal end of the ball may include a nub or nipple 142. Indeed, such a feature is advantageous in a construction as illustrated in FIG. 7.

In this side-sectional view, the braid matrix is shown inverted (or everted) at fold 24. A band 144 is set between the inner and outer braid layers. The band closes the end and servers as a marker (especially when it comprises Pt). An adhesive compound 146 (e.g., LOCTITE 3311 or 4014) may be used to fill any residual lumen within the fold aperture. As with the other implants (including those in FIGS. 4A and 4B) the implant may include a recapture profile section 52 at its proximal end, adjacent the hub 42. Likewise, it may include a hub port 54.

Otherwise, both ends of the implant may be closed/plugged with an adhesive or otherwise. Without a delivery system access port, the implant may be delivered using a simple pusher (vs. being fully retrievable and/or repositionable). So-configured, no proximal hub is required either. Indeed, the braid may simply be trimmed and shape set to come together and/or be secured by welding, adhesive or otherwise at the proximal end.

Figure 8A:
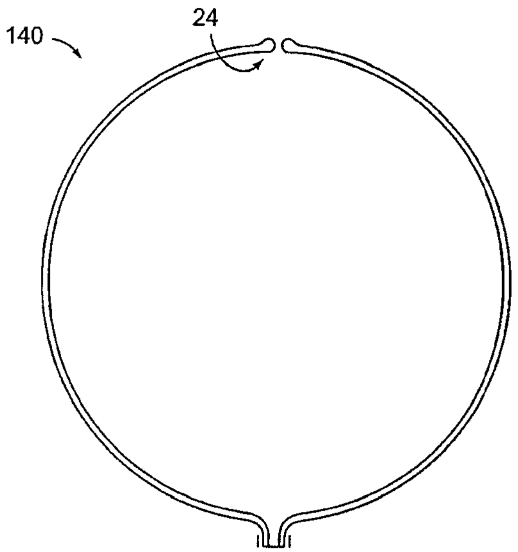
FIGS. 8A and 8B are side-sectional views of an implant shown in stages of manufacture.
Figure 8B:
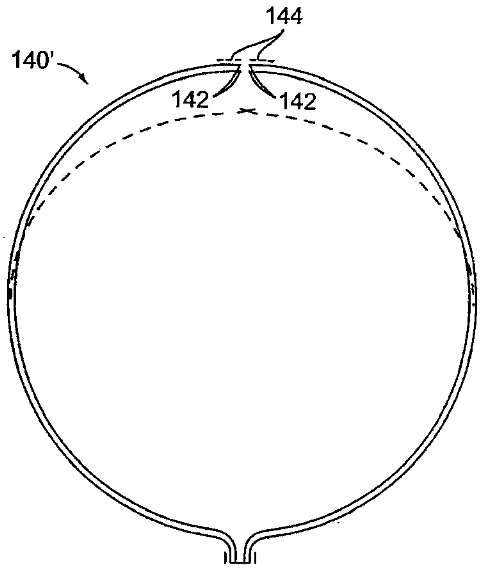

Another optional aspect of the invention is illustrated in FIGS. 8A and 8B. Namely, a folded layer implant 140 is first formed without taking steps to minimize the bend radius at the braid fold 24. While still usable, it may instead be desired to trim off the folded layer to produce a modified implant 140' as shown in FIG. 8B. Doing so eliminates the bulk, and also changes the implants delivery properties as may be desirable in certain circumstances. The implant becomes more radially compliant and able to fit a wider range of aneurysm sizes because ends 142 of the braid can pass by one another rather than bottoming-out. As such, the same implant 140' can fill a smaller volume without necessarily extending from the neck of the aneurysm as indicated by dashed in FIG. 8B.

In any case, because of the original construction technique utilizing one tube of braid and folding it over to produce two layers, the (now-separated) layers are well matched to predictably expand and contract. Moreover, once any profile-limiting bends are removed (e.g., by cutting, grinding, etc.) the layers can be reconnected if the adjustability feature described above is not desired. A urethane coating layer 144 or other adhesive (advantageously including radiopaque Barium or Tantalum powder) may be used locally to accomplish such action without a resulting increase in delivery profile.

Still, maintaining the fold in an implant offers numerous advantages in other circumstances—especially when it is formed in such a manner that minimizes wire bend radius/profile. Namely, implants including the fold may offer better size integrity and radial force in circumstances when desired, eliminate any loose fibers at an end of the implant without further processing (such as by polymer application), provide a pocket for a marker and/or tie to suspend a marker, etc.

Figure 9:
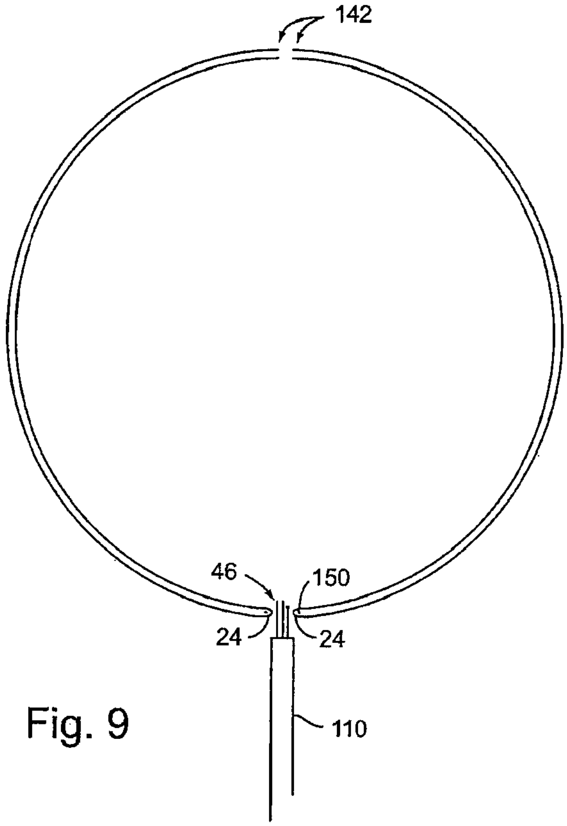
FIG. 9 is a side sectional view of an implant in which the folded section is to be utilized at a proximal side of the device.

Moreover, it is to be recognized that the folded end of the implant will not necessarily be set at the distal end of the device. Rather, the folded section 24 may be utilized at a proximal side as shown in FIG. 9. And the aperture 46 formed by the folded section (when held by a ring, band or tie 150) provides a delivery system 110 interface. The opposite end of the implant may have an inset hub (e.g., as illustrated in FIGS. 4A and 4B) or terminate with trimmed ends 142 much like that shown in FIG. 8B (with or without incorporated polymer) or be otherwise configured.

In any case, FIGS. 10A-10D illustrates one approach to constructing a folded-section implant in which the profile of the fold is minimized. As will be appreciated by those with skill in the art, elements of the method may be applied to various of the implant configurations discussed herein.

Figure 10A:
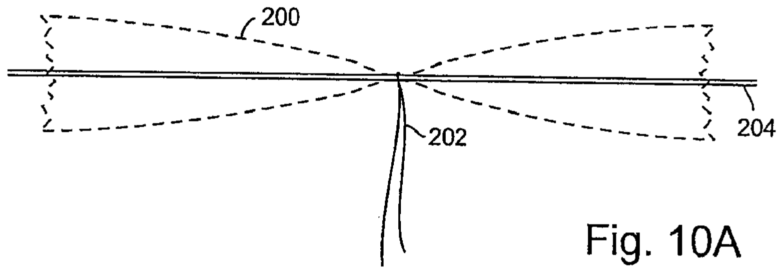
FIGS. 10A-10E are side views illustrating stages of a folded-section braid ball implant manufacture.
Figure 10B:
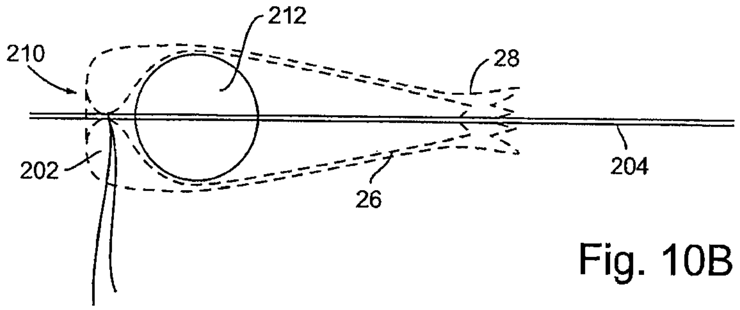

In these figures, FIG. 10A shows a section of braid 200, tied with suture 202 upon a mandrel 204. The tie is offset from where the braid is cut so that when the braid is inverted as shown in FIG. 10B, the outer layer 28 extends past the inner layer 26. A loose fold 210 is developed and the braid surrounds the implant shaping form 212.

Figure 10C:
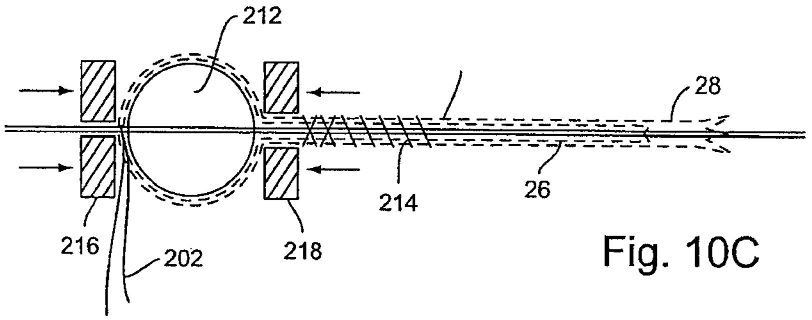

In FIG. 10C, the braid is stretched and secured by wrap 214 (typically Pt or Stainless Steel wire) around the ball form 212. Compression forms 216, 218 are also shown (held by fixturing as indicated by arrows). Fold-side form 216 compresses the fold to a minimum profile during heat setting (e.g., for Nitinol braid at 550° C. for 5 minutes). In this process, the original tie 202 (if made of suture) burns away removing any impediment for achieving a zero or near-zero radius bend at the fold. Opposite form 218 my define a sharp shoulder section (for when that end of the ball is to be trimmed and used as the distal end, in a "floating-layer" ball as described below, etc.) or shape a recapture profile into the braid.

Figure 10D:
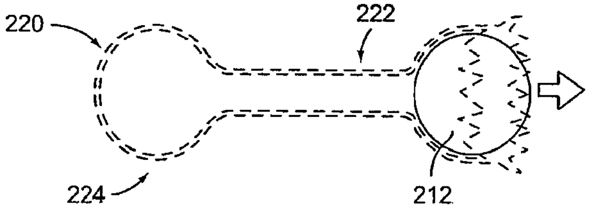

After any such shape-setting, a device perform 220 is ready once the internal form is finally removed as illustrated in FIG. 10D. During this process, the ends of the braid are forced open and typically lose braid integrity/engagement. So that such action does not adversely affect the implant integrity, a "tail" 222 incorporated in the perform 220 should be sufficiently long (i.e., often about 2 cm or more) so as to avoid any damage from unraveled braid ends impacting the intended body 224 of the implant.

If the implant is formed from braid that includes an oxide layer, the perform is next etched, then passivated. However, if pre-etched wire is employed in braiding and any heatsetting performed in a salt pot, vacuum furnace, or using other equipment to minimize oxide formation, the perform may simply be subject to Nitric acid passivation.

Figure 10E:
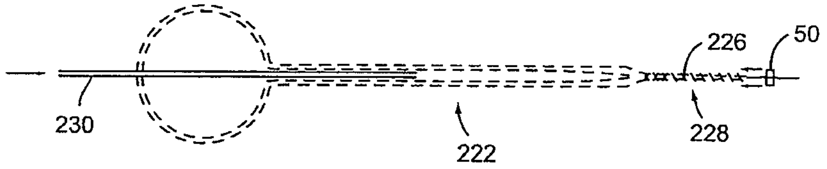

Even if additional intermediate process steps are employed, FIG. 10E illustrates a manner in which a band 50 may be added in forming a hub. Specifically, after tying the outer layer 28 with a wrap 226, the band may be threaded over this section. Without the inner layer underneath, the tied section 228 fits within the band 50 such that the band can be sized to tightly fit around both layers of braid (and an optional mandrel 230—the utility of which is discussed below) when advanced to a point adjacent the implant body 224.

Figure 11A:
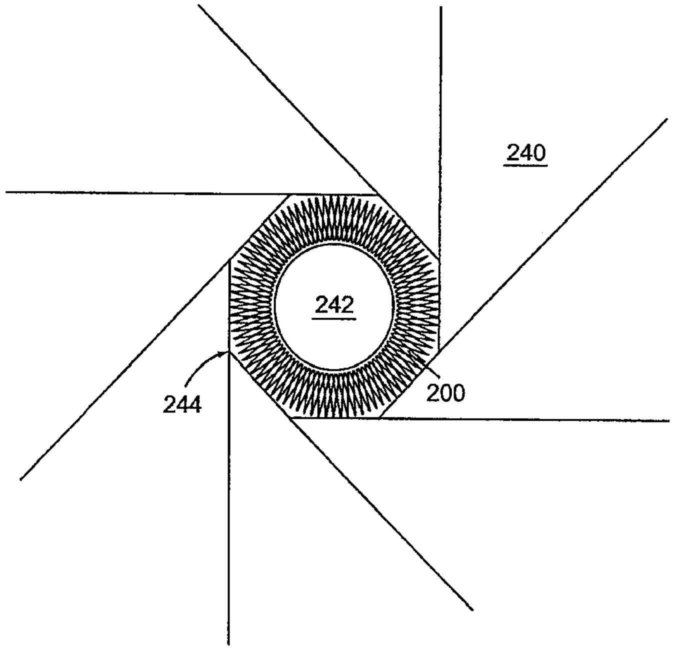
FIGS. 11A and 11B are end views diagrammatically illustrating a technique for presetting the shape of the implant fold.
Figure 11B:
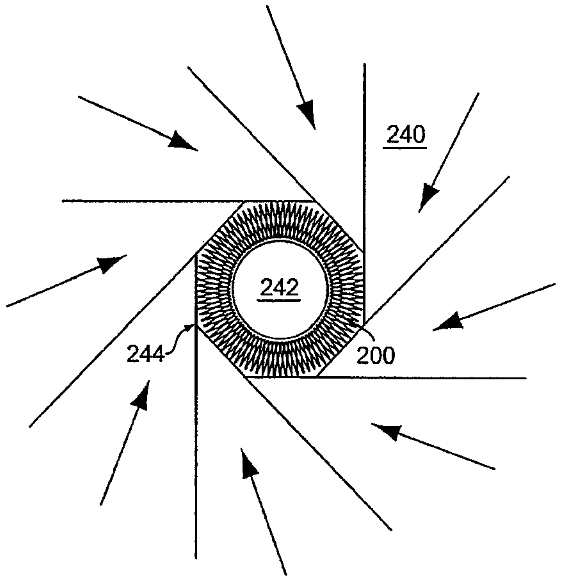

An alternative approach to compression-forming the fold during perform shaping to achieve a minimum radius bends in the braid wire is presented in FIGS. 11A and 11B. These figures illustrate a technique for presetting the shape of the implant fold. In FIG. 11A, wedges 240 of a crimper device (e.g., as available through Machine Solutions, Inc. and others) receive braid 200 that is folded over to define a plurality of bends. A mandrel 242 is advantageously set inside the braid. The mandrel limits compression of the braid tube, requiring the bend radius tighten when the aperture 244 formed by the wedges is closed as indicated in FIG. 11B. The shape of the fold is set by heat and/or a combination of strain and heat. The heat may be applied by a torch, within a furnace or, advantageously, by running current though the mandrel. In another approach, a multi-element chuck or collet type device is employed in a similar fashion to the crimper wedges illustrated above.

So-shaped, the overall implant may be formed largely as described in connection with FIGS. 10A-10D without the use of the suture tie or compression form 216. Instead, a permanent fine-wire tie that remains throughout the process may be employed to close the folded end of the ball. This tie can be installed simply by flipping back the folded braid to expose the bends. Alternatively, it can be threaded through and around the bend folds with a needle and tied.

Figure 12A:
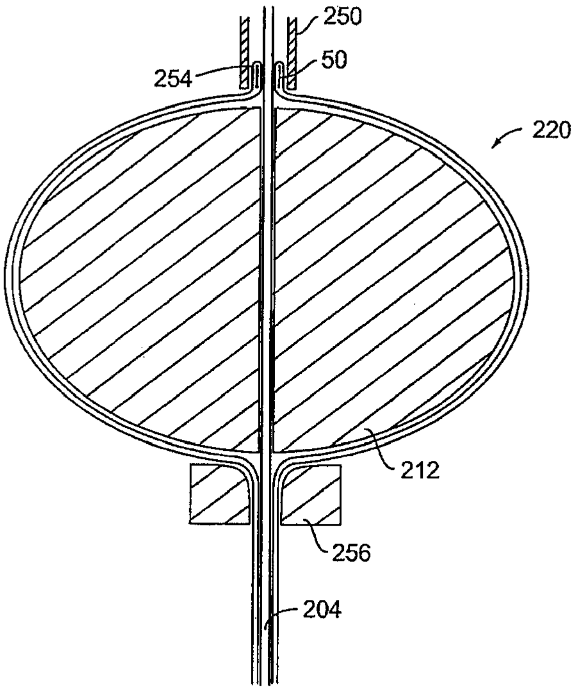
FIGS. 12A and 12B are side sectional views illustrating folded-section braid ball implants with associated tooling for setting their shape.
Figure 12B:
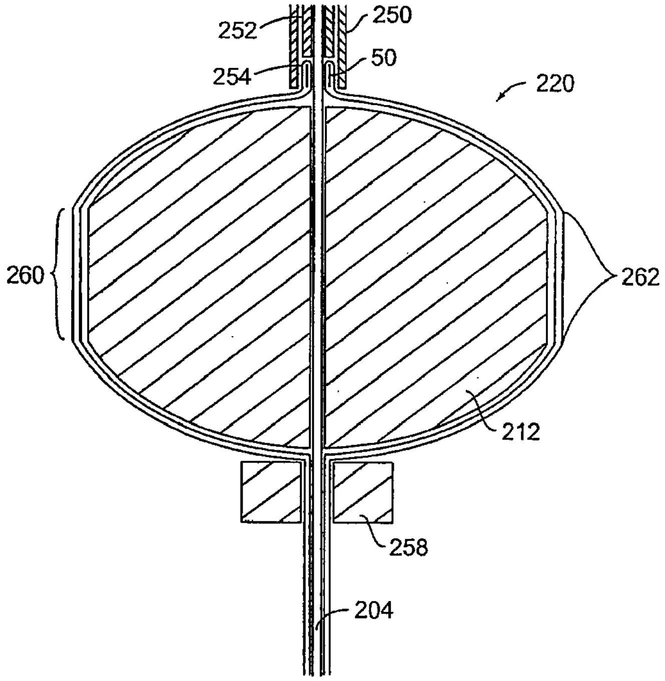

Pre-treating the fold or compression forming it during heatsetting the bulk of the implant is advantageous especially for those cases in which the region adjacent the fold is to be dome shaped. However, when a nubbin is acceptable in the device design given its intended use (e.g., PVO) FIGS. 12A and 12B illustrate another approach. Specifically, a hypotube 250 (or other shaped form including a pocket) is placed over the braid where the braid is trapped between a band 50 and/or the band and mandrel 204 as shown. In addition, as shown in FIG. 12B, a second hypotube 252 (or surface in a form pocket) can abut the distal bend point 254 to further constrain the braid for precision shape setting.

As for setting the remaining shape of the implant or its perform 220, FIG. 12A illustrates the use of a proximal trumpet shaped form 256 to set a smooth recapture profile. In FIG. 12B, the proximal form 258 sets a tight or sharp radius. Such a shape may be desired to achieve higher radial force in the implant due to greater local bending strain.

The implant shown in FIG. 12B seeks to achieve improved anchoring over that in FIG. 12A by virtue of the other noteworthy features illustrated in the drawings. Namely, the cylindrical band 260 shape set in the implant along the otherwise ovular device shape produces edges 262 that interact with vascular tissue with increased local stress to improve anchoring.

Both implants still share a flattened/reduced aspect ratio relative the spherical ball implants previously pictured. Such an aspect ratio allows for greater oversize for anchoring the self-expanding implants in vessel for a resulting length of device. This fact is advantageous given that the focal length of occlusion is often important in treating neurovascular defects in order to inadvertently block adjacent perforator/branch vessels in PVO applications.

Figure 13A:
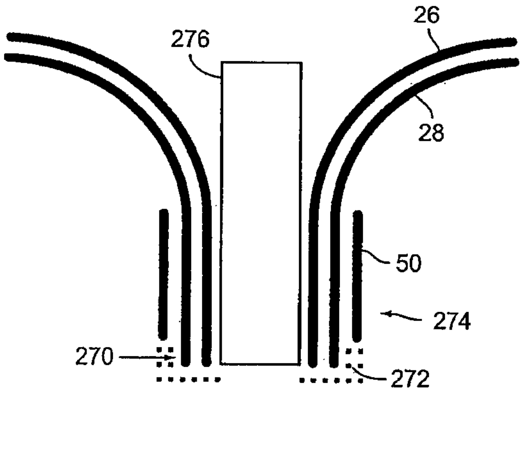
FIGS. 13A and 13B are partial side-sectional views illustrating alternate braid/band affixation approaches.
Figure 13B:
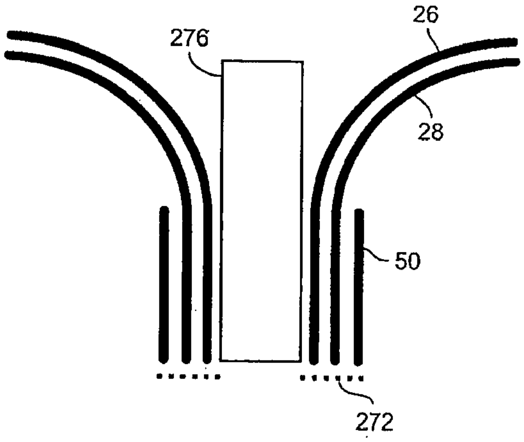

Whatever the form of the implant, when a hub is included to secure the braid filaments, certain affixation challenges must be addressed. The hub must be securely fastened to the braid and it may be necessary to minimize the length of the feature. FIGS. 13A and 13B are partial side-sectional views illustrating alternate braid/band affixation approaches. In FIG. 13A, band 50 is set past a trim line for the braid. The small resulting tail 270 provides a surface across which glue 272 can be applied. Once cured (e.g., by UV application) the adhesive is entrained in the braid and forms an edge 274 over which the band cannot pass. If glue is not used, then the braid may be melted with a laser to similarly form an interference feature for the band. Such laser application may weld the braid to an internal band 276 if one is employed. The laser may be applied in a radial direction around the braid, or axially across the trimmed face of the braid.

Especially when utilizing laser energy, an alternative approach as illustrated in FIG. 13B may be employed. Here, by applying laser energy directed axially across the edge of the band(s) and the face of the braid, all of these may be welded together. Even if so-welded, the resulting face may be sealed with polymer adhesive 272.

Figure 14:
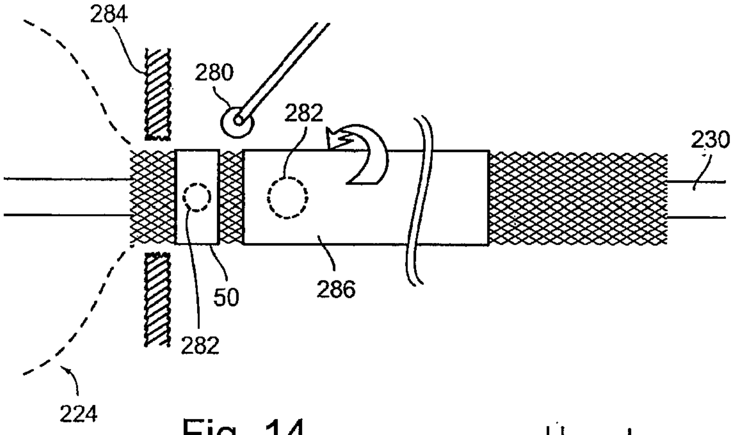
FIG. 14 is a partial side-sectional view illustrating a hub-gluing approach.

FIG. 14 illustrates yet another approach to hub fixation. Here, wicking is relied upon for glue/adhesive penetration through the braid under the band to form a bond. A bead 280 of glue is applied to an exposed segment of braid 200 adjacent the band 50. A non-stick (e.g., PTFE coated) mandrel 230 may be situated inside the braid to precisely define a lumen within the glue-impregnated braid. The lumen advantageously operates as a delivery system port. Once the adhesive is cured and the mandrel is removed, a precisely-sized composite wall structure is produced.

The adhesive may be applied evenly around the braid by rotating the assembly as indicated. Other approaches may be utilized as well. In one such approach a plurality of optional access windows 282 may be included in the band to receive and disperse adhesive. Adhesive is also optionally wicked away from the braid 200 by a paper card or absorptive fiber pad 284 (or removed by other means) so that any excess of wicking/flowing adhesive utilized to ensure braid lumen coverage and/or band 50 adhesion does not interfere with the self-expanding action of the implant body 224.

Use of an inner band 276 is also optional. While it occupies space that the braid-and-glue only lumen conserves, including an inner band in the hub assembly 42 may sometimes be desirable for the detachment system interface.

Use of an adjunct hypotube 286 is also optional. This tube, however, offers a useful grip or handle on which to clamp for subsequent trimming. Especially for such use, a thick-walled (e.g., about 0.005" or greater) tube may be desirable because of additional stability it will yield. As with the band which becomes part of the implant, hypotube 286 may include one or more access windows 282 for adhesive application.

Figure 15:
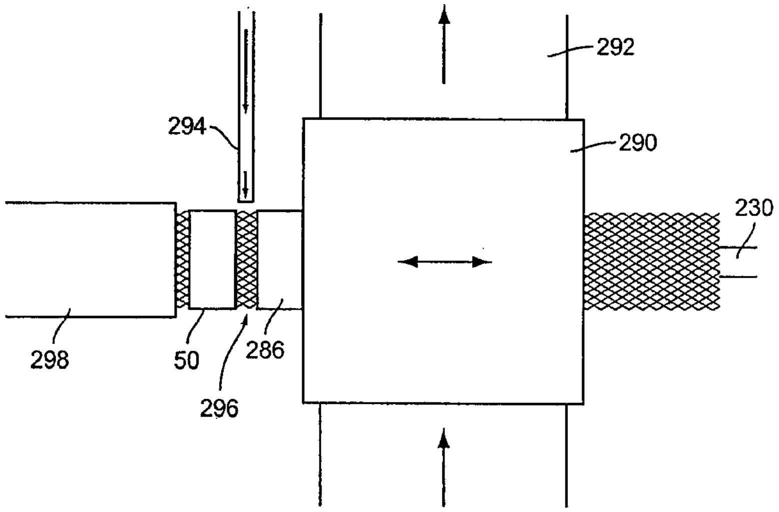
FIG. 15 is a partial side view showing a hub-trimming approach.

For trimming an implant perform 220 (however it is shaped), FIG. 15 illustrates an approach that coordinates well with the hub affixation approach illustrated in FIG. 14. Specifically adjunct hypotube is captured in a fixture 290 mounted on a slide 292. Lateral adjustment may be provided for in order to align a saw blade 294 (typically a 0.004-0.010 inch diamond-coated wheel) with a gap 296 established between the band and hypotube 286 grip. Once aligned (the cut line may be at the gap, or the band itself may be cut down) the implant is trimmed-off. To aid in handling, the implant may be at least partially constrained in a sheath 298 as shown. A precision cut/trim allows for a band (as trimmed or initially installed) as short as about 0.010 inch in height. A more conservative size (e.g., about 0.020 inch in height) may however be desired to ensure braid capture and detachment system robustness.

After the cut is made, the hub length may be further reduced by grinding its face. After mandrel removal (also cut-off in the trimming procedure) and cleaning in an ultrasonic bath, the hub face may be sealed with adhesive.

Figure 16:
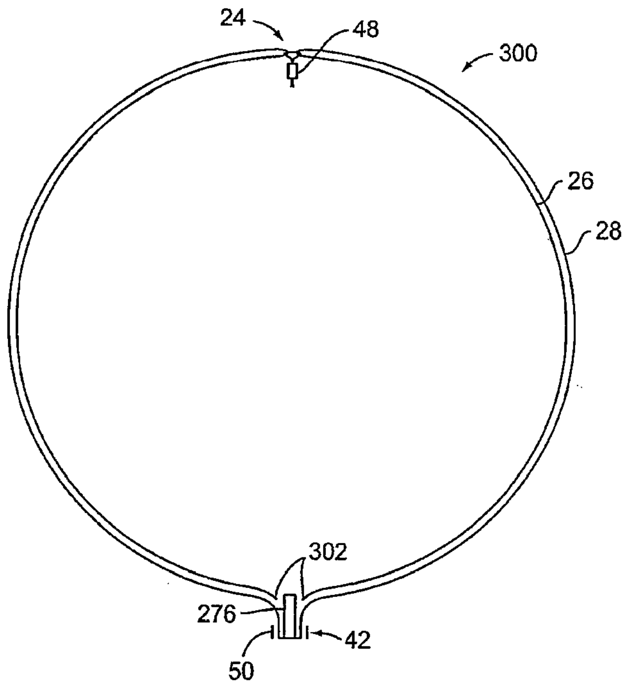
FIG. 16 is a side-sectional view illustrating another folded-section braid ball implant variation.

Produced using any of the referenced hubbing techniques, another implant variation 300 is illustrated in FIG. 16. Additional steps unique to its manufacture are presented in FIGS. 17A-17D.

The implant differs from those discussed above in that it includes a layer of braid that is not secured at each end of the device. Rather, the inner layer 26 "floats". Its presence augments implant density, but its fibers adjacent the hub 42 are not forced to bend when the ball is compressed in a sheath for delivery and/or recapture. As such, relatively less force is required for recapture, even when the braid is bent at approximately 90 degrees upon exiting the hub (i.e., without the proximal end of the implant body 224 including a recapture profile in the design).

Figures 17A, 17B, 17C, 17D:
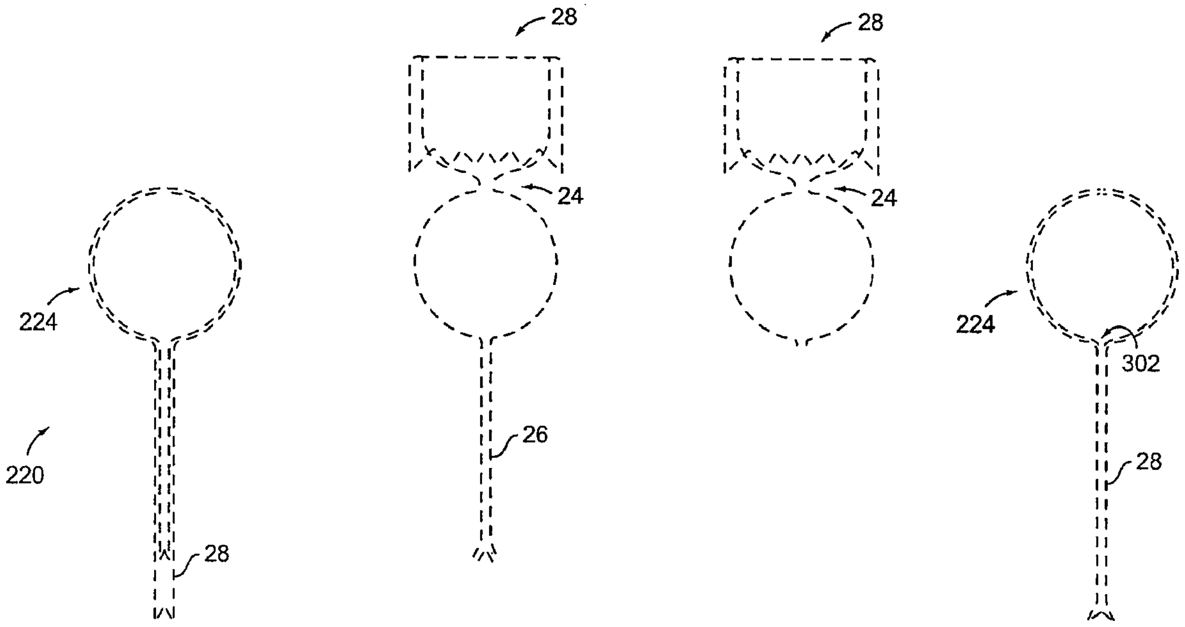
FIGS. 17A-17D are side views illustrating stages of the FIG. 16 embodiment manufacture.

To produce a ball with the inner braid ends 302 proximate to the hub where the density of the outer braid is highest and best able to prevent individual filaments from the inner layer poking through the braid matrix, an elegant set of manufacturing steps are carried out. Specifically, after starting with an implant perform 220 as shown in FIG. 17A, the outer layer of braid is pulled or pushed off of the intended body 224 of the implant as shown in FIG. 17B. The inner layer of braid is trimmed as shown in FIG. 17C. Wire cutters, scissors or other means may be employed. Finally, the outer layer is returned to its original position as shown in FIG. 17D and the implant perform is further processed.

Such further process may include banding/hubbing, trimming and/or tying the fold aperture closed. However, such tying may advantageously be performed prior to restoring the position of the outer braid while the fold 24 is exposed per FIG. 17B/17C.

Figure 18:
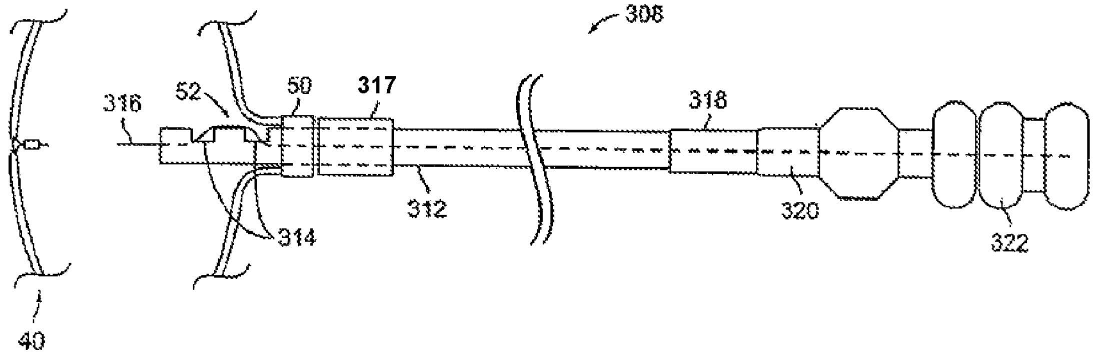
FIG. 18 is a side view of a delivery system variation suitable for use in the present invention.

Whatever techniques are employed in their construction, the implants are advantageously mounted to a releasable pusher. Delivery system 308 in FIG. 18 is includes a hypotube shaft 312 with cut-out windows 314. The window 314 adjacent the ball hub is critical, the other merely advantageous. A core member 316 (advantageously Nitinol ribbon) exits the proximal window 314 or cutout and re-enters at the second 314. A shoulder/bumper 317 attached to the hypotube abuts a proximal end of the hub 50 to push the implant 40. Alternatively, an external sleeve (not shown) running to the length of the hypotube to a delivery system strain relief 318 and/or hub 320 may be provided. To permit retracting the implant into the delivery catheter (not shown), core member 316 engages the inner surface of the hub lumen (hidden) to retain the implant.

To allow release, the core member is withdrawn into hypotube 310 clearing each of the windows 314 by pulling finger grip 322. At which point, the hypotube may exit the hub port 54 by withdrawing the pusher.

Figure 19A:
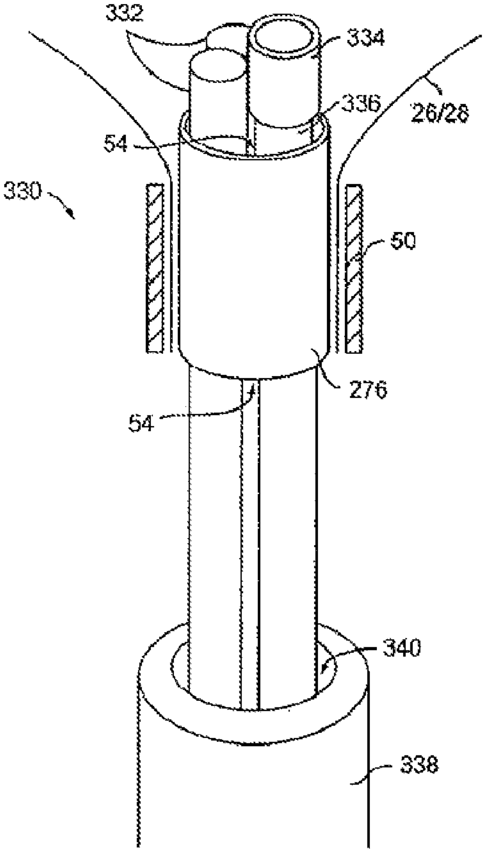
FIG. 19A is a partial side-sectional view of a distal end of another delivery system variation suitable for use in the present invention.
Figure 19B:
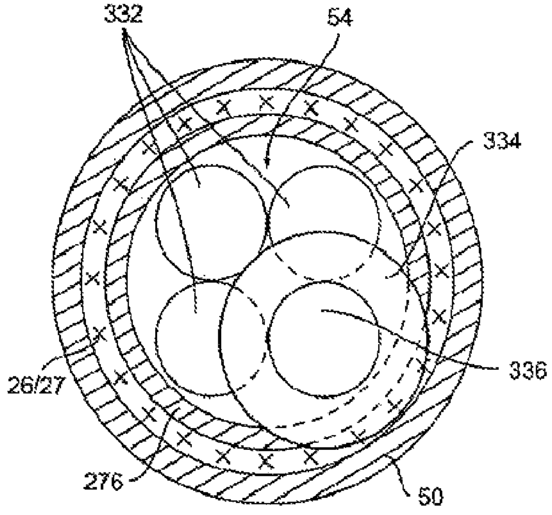
FIG. 19B is an end view from within the implant of the system shown in FIG. 19A.

Another detachable delivery system 330 is illustrated in FIGS. 19A and 19B. It is a fully co-axial design in which control wires 332 are pulled to release interference of a head 334 mounted on an anchor wire 336 otherwise unable to pass through a hub port or lumen 54. Because the wires are pulled straight out and only position the anchor wire head to ensure interference (clearly illustrated in FIG. 19B) minimal effort is required. EPTFE coating over at least the control wires is also useful.

The control wires 332 may extend to or past the anchor wire head 334 (the former case illustrated in FIG. 19A). Another option is to limit the control wire length to that of any inner band 276 or overall hub 42 height dimension (as illustrated in FIG. 19B). Note also: FIG. 19A shows a gap between a pusher sleeve 338 and implant hub 50. This representation is for illustration purposes only.

In any case, each of the pusher sleeve lumen 340 and the implant hub lumen/port 54 is preferably sized so that the wires (control wires 332 and anchor wire 336) are received in a close-packed arrangement. In this manner, the implant and pusher sleeve serve as a guide eliminating loading difficulties associated with the wires becoming braided or entwined. Also for loading the system, the anchor wire is typically tensioned to a very slight degree (prior to simple gluing into a handle or using a bias spring incorporated in the handle design) to ensure any gap between the implant and pusher is closed and remains closed in use.

Figure 20A:
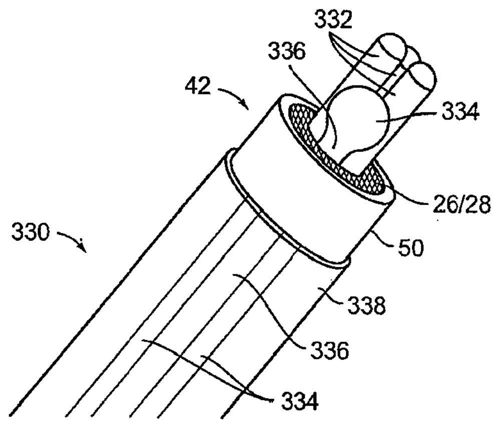
FIGS. 20A-20F are partial perspective views of implant detachment with a system constructed according to the approach shown in FIGS. 19A and 19B.
Figure 20B:
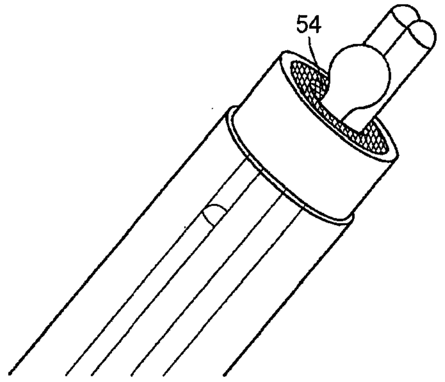
Figure 20C:
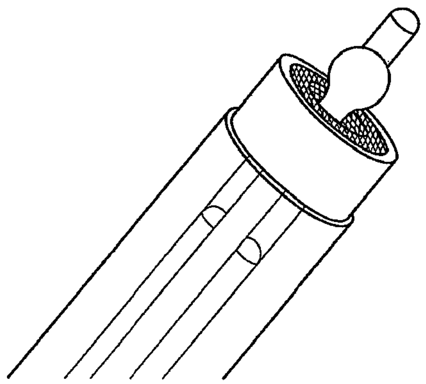
Figure 20D:
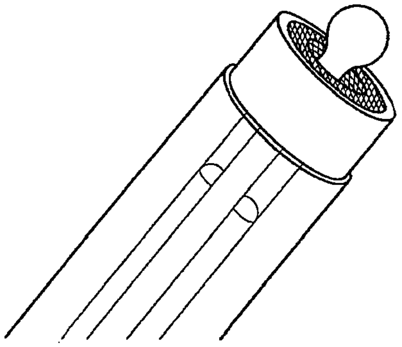
Figure 20E:
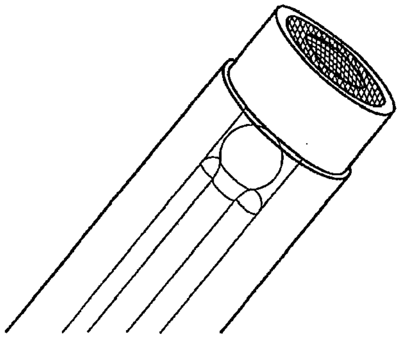
Figure 20F:
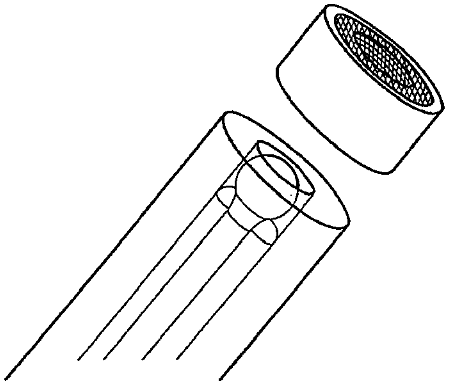

FIGS. 20A-20F illustrate a variation of delivery system 330 is use. The distal end of the detachment system is shown with the hub 42 portion of an implant. FIG. 20A shows the pusher interlock engaged. FIGS. 20B-20D illustrate sequential withdrawal of the control wires 332. Anchor wire 336 may also be individually withdrawn as shown in FIG. 20E. However, it may instead by withdrawn with the detachment system sleeve 338. Indeed, it may be affixed to the sleeve. Still further, it is to be recognized that the control wires need not be pulled one at a time. They can be actuated together. In any case, complete implant separation is illustrated in FIG. 20F.

Figure 21:
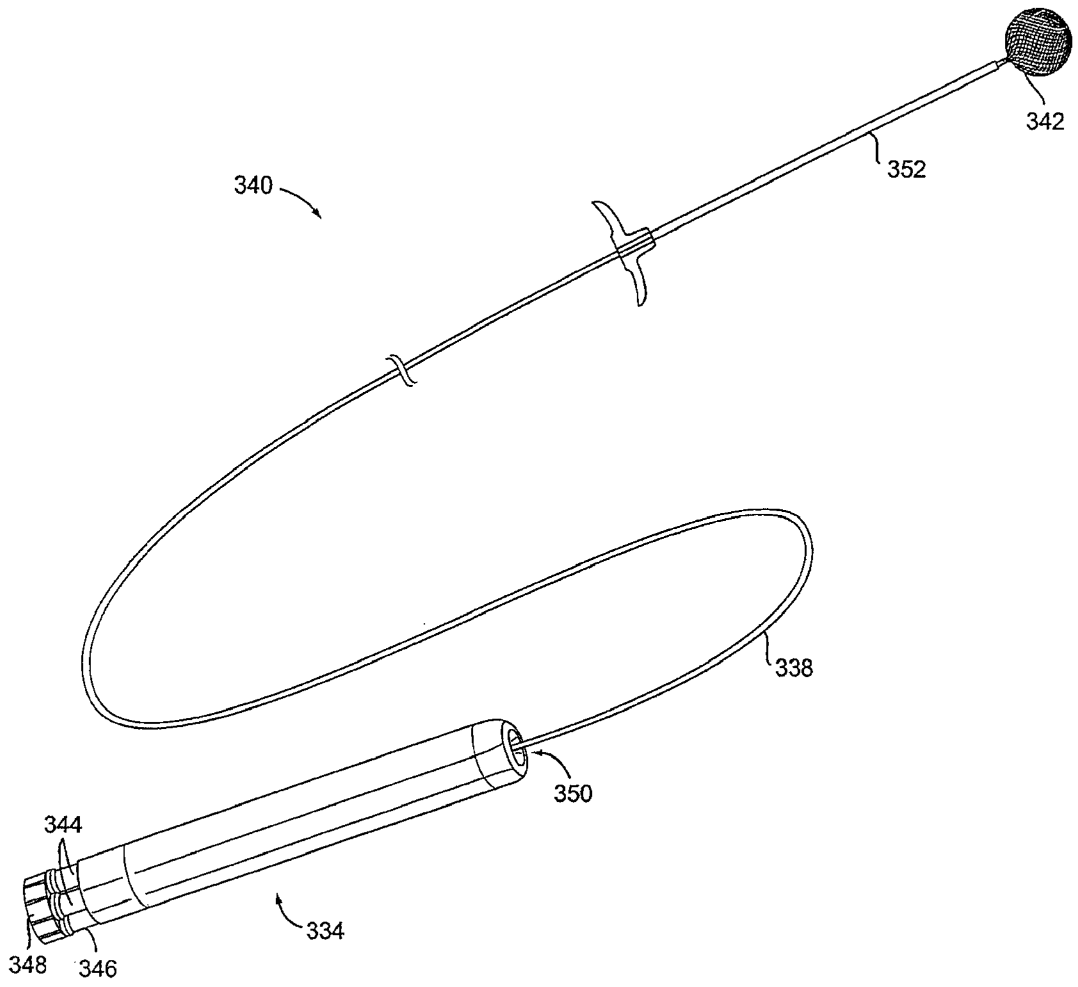
FIG. 21 is a perspective view providing an overview of a treatment system according to the present invention.

Finally, FIG. 21 presents an overview of a treatment system 340 including an implant 342 and handle 334. Either one or both of these may be constructed according to the teachings herein. The handle 334 shown includes three knobs. Two knobs 344 are connected to control wires (hidden from view), and the last knob 346 to an anchor wire (hidden from view). A removable locking cap 348 may be included in the handle design as well as a strain relief section 350. The catheter/pusher shaft 338 may comprise a simple extrusion (e.g., PTFE, FEP, PEEK, etc.) or may be constructed using conventional catheter construction techniques and include a liner, braid support and outer jacket (not shown). A loading sheath 352 is typically provided over the pusher shaft. Advantageously, the loading sheath is splittable as is model shown.

After removal from sterile packaging (not shown), the implant is pulled into the loading sheath 352. The loading sheath is received within the hub of the catheter to be used for implant delivery and the implant is advanced into the catheter. Then, the implant may be advanced to and deployed at a treatment site. Or it may be retrieved in exchange for another size implant, else repositioned if desired prior to ultimate detachment like that illustrated in FIGS. 20A-20F.

The subject methods may include each of the physician activities associated with implant positioning and release. As such, methodology implicit to the positioning and deployment of an implant device forms part of the invention. Such methodology may include placing an implant within a brain aneurysm, or at parent vessel targeted for occlusion, or other applications. In some methods, the various acts of implant introduction to an aneurysm or parent vessel are considered.

More particularly, a number of methods according to the present invention involve the manner in which the delivery system operates in reaching a treatment site, for example. Other methods concern the manner in which the system is prepared for delivering an implant, for example attaching the braid ball to the delivery system. Any method herein may be carried out in any order of the recited events which is logically possible, as well as in the recited order of events, or slight modifications of those events or the event order.

Also, it is contemplated that any optional feature of the inventive variations described may be set forth and claimed independently, or in combination with any one or more of the features described herein. Reference to a singular item, includes the possibility that there is a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of the claim language. Use of the term "invention" herein is not intended to limit the scope of the claims in any manner. Rather it should be recognized that the "invention" includes the many variations explicitly or implicitly described herein, including those variations that would be obvious to one of ordinary skill in the art upon reading the present specification. Further, it is not intended that any section of this specification (e.g., summary, detailed description, abstract, field of the invention) be accorded special significance in describing the invention relative to another or the claims. All references cited are incorporated by reference in their entirety. Although the foregoing invention has been described in detail for purposes of clarity of understanding, it is contemplated that certain modifications may be practiced within the scope of the appended claims.

Especially for aneurysm treatment, but also for either one of the aforementioned treatments, the form of the ball is very important. In particular, the density of the device is paramount in applications where braid itself is intended to moderate or stop blood flow—allowing thrombosis within a volume formed by the ball.

According to the present invention, braid-ball type implants are provided in braid of sufficient density to moderate blood flow within the volume of the implant. Upon thrombosis, flow thereto is stopped. Alternatively, a blood-barrier covering can be applied to the filamentary structure to immediately stop blood flow into the vascular site, in which the implant volume is set.

In either case, to form thrombosis within the volume of the ball, the filaments of the braid matrix permit filling of the implant with blood when emplaced at a vascular treatment site. This blood then thromboses due to the flow-disruption effect(s).

Unlike Nitinol tube-cut cages that may be suitable for (or assist) in coil retention, the ball devices are adapted to work alone—or in combination with each other to effect a complete treatment. As such, high density braid/mesh is typically required. Namely, braid having at least about 48 ends, typically set at about 90 degrees or greater, in diameters from about 4 to about 8 mm may be employed. At larger diameters (e.g., about 6 to 12 or more), more wire ends (e.g., 64, 72 and upwards) may be employed in forming the balls.

Suitable braid for constructing the balls may be obtained from Secant Medical, Inc. Wire diameters may be in the range of about 0.001 to about 0.003 inches, depending on desired delivery profile (which is typically less than about 0.050 inches). The braid forming the balls may incorporate only one size wire, or may be formed with multiple sizes.

The wire is preferably superelastic NiTi alloy. The metal may be a binary alloy or a ternary alloy to provide additional radiopacity. Alternatively, radiopaque platinum fibers may be included in the braid, or the wire may comprise platinum or gold core Nitinol DFT. Otherwise, wraps or bands (preferably Pt) used to secure the braid wire may serve as the sole radiopaque feature(s).

In any case, the construction approaches described herein enable producing these useful devices. Whether comprising braid alone, or incorporating some further blood-barrier covering (such as a thin urethane film as may be applied by Hantel, Inc. or others), the use of braid presents numerous challenges in managing the termination of multiple wires and in forming the desired structures.

Also included in the invention are detachable implant pushers that utilize a resistance wire heater to thermally sever a suture associated with the implant to effect release. As distinguished from known approaches where an implant is retained by a loop connected back to a delivery system pusher that is withdrawn with the delivery system, the present invention contemplates a leave-behind tether.

Further details, variations, modification and optional features of the invention may be appreciated by review of any of the incorporated patent applications. However, the priority date and subject matter included in the appended claims rely solely on the subject matter filed in U.S. Provisional Patent Application Nos. 61/046,670 and 61/046,594, the earliest patent applications (each filed Apr. 21, 2008) on which U.S. patent application Ser. No. 12/427,620 relies. Selected figures from the '670 and '594 application and all of text from the '594 application—all—incorporated by reference in the parent application hereto is reproduced herein.

Implants

Referring to FIGS. 22-25F, a filamentary implant 402 is formed out of braid to treat vascular sites. Interwoven filaments 404 form a braid matrix 406 that define a self-expandable occlusion device.

Figure 22:
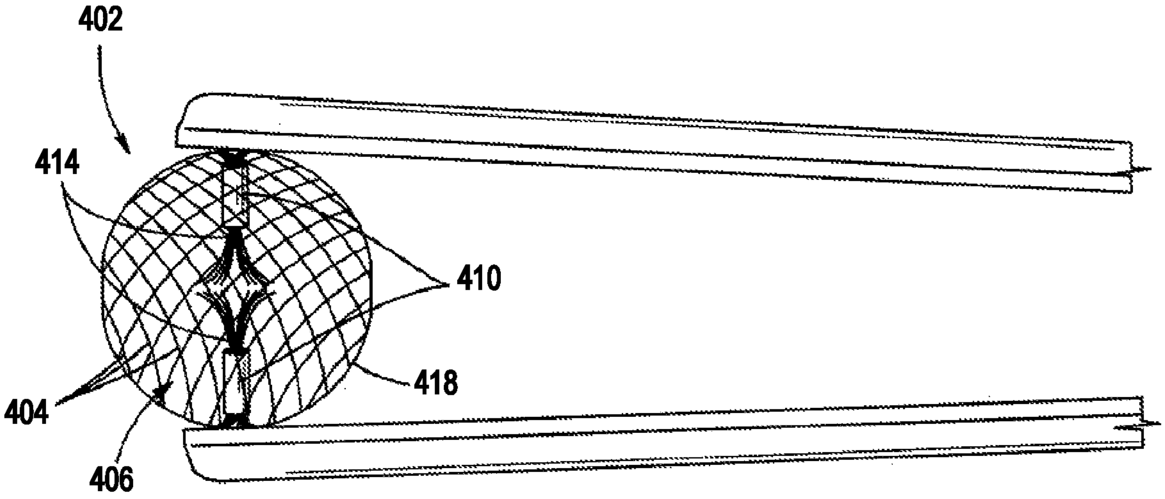
FIG. 22 is a photograph taken from U.S. Provisional Patent Appl. No. 61/046,670 (incorporated herein by reference) demonstrating actual reduction to practice of a single-layer braid ball device made according to the present invention.
Figure 23A:
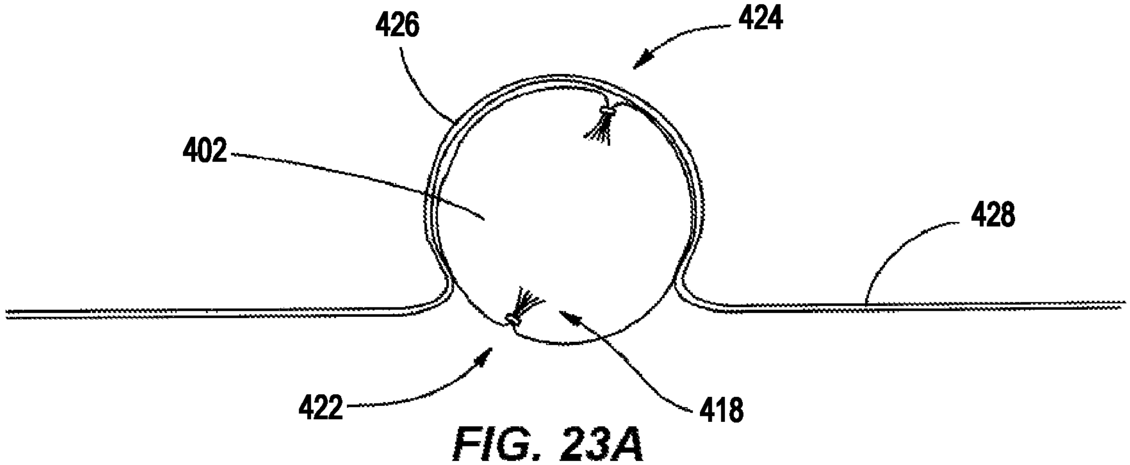
FIGS. 23A and 23B are side-sectional views of the braid ball in isolation and in use, respectively.
Figure 23B:
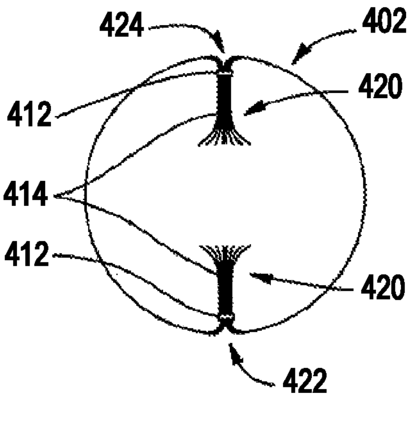

As single layer of the braid is provided in which ends of the braid are secured and managed to provide an atraumatic interface. Specifically, ties 410 (as illustrated in FIG. 22) or bands 412 (as illustrated in FIGS. 23A and 23B) secure the ends 414 of the braid from which the implant is constructed.

In the implant variation pictured, the expanded configuration defines an ovoid or roughly spherical shell 418 that is permeable to blood. The braid defining the proximal and distal ends of the implant turns or curves inward to a point where it is secured within the periphery of the shell.

The inversion of the braid provides recessed securement of the braid resulting in atraumatic ends of the implant. The braid filaments optionally extend beyond the securing/securement features in order to define wire filament "tufts" 420 that will further promote thrombosis of blood that enters the ball upon deployment within a patient's vasculature. However configured in regard to braid filament end securement and termination, inset ends of the braid (proximal and distal insets 422/424, respectively) are demonstrated when the implant is in an expanded state to fill an aneurysm 426 off of a vessel 428.

Delivery Systems

Figure 24:
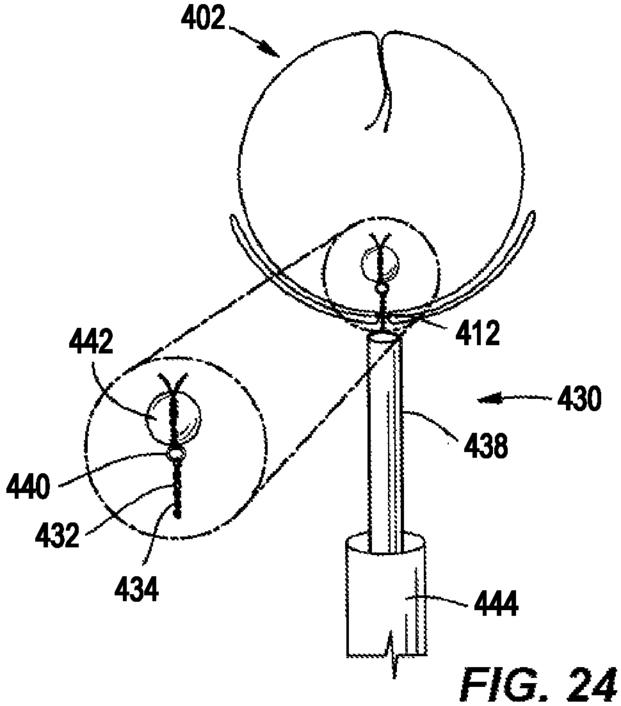
FIG. 24 illustrates a suture-melt resistance heater pusher for implant delivery.

FIG. 24 illustrates a detachable catheter/pusher 430, optionally, for use in the present invention. Generally, it includes a resistance wire bridge 432 across insulated conductors 434 (a typical construction). What is unique is that the conductor wires are twinned/twisted along a length of the delivery pusher shaft 438 as shown. This configuration alleviates bending bias/preference. Upon application of voltage, the tip thermally severs the polymer filament (e.g., suture 440) in contact therewith. At least the suture portion is received within the implant 402 (e.g., passing through a braid-securing band 412). The suture is retained in/with the implant upon actuation to release the implant by cutting through the suture with heat. A ball stop 442 that is tied to the suture and retains the filament in/with the implant is also illustrated. Finally, pusher 430 is shown received within a typical microcatheter 444 for vascular access, after passage therethough. Note also, other advantageous delivery system are referenced and described in the incorporated patent application.

Methods of Manufacture

Included in the invention is a method of manufacture including tying-off or otherwise securing a second end of a braid within an interior volume of a ball where other approaches would be impracticable. The technique may be employed in creating the balls (be they spherical or ovaloid in cross-section, etc.) out of one continuous section of braid. In so doing, joints and other delivery profile-increasing features are avoided—as well as potential areas for failure. Accordingly, the subject implants are extremely robust and fully recoverable to their aneurysmal shape as is required when they are delivered through a catheter in low profile. Robust shape recovery is required in treatments targeting distal vasculature, especially the tortuous neurovasculature encountered in human brains.

Figure 25A:
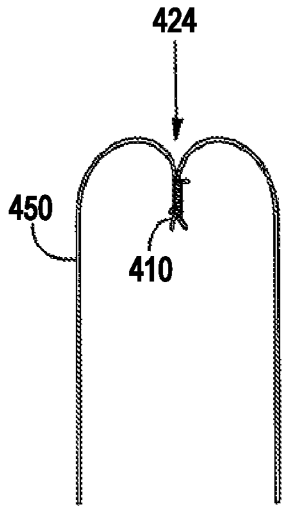
FIGS. 25A-25F illustrate a production path of one implant embodiment encompassed by the current invention.
Figure 25B:
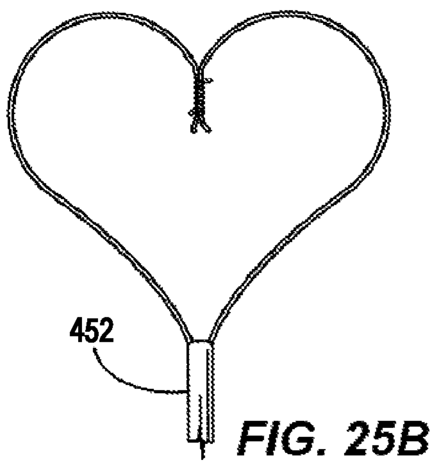
Figure 25C:
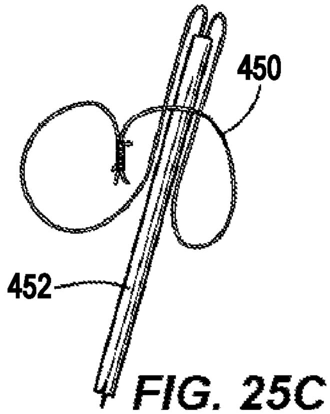
Figure 25D:
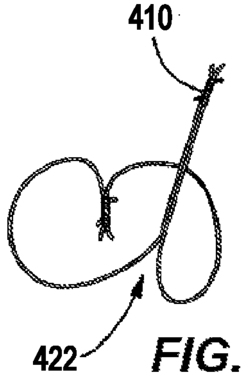
Figure 25E:
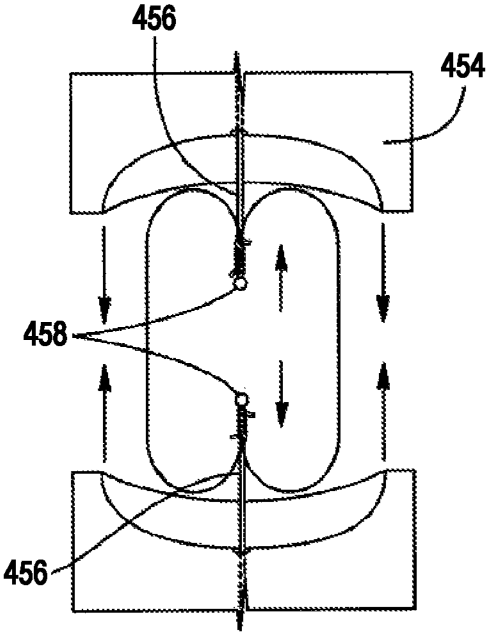
Figure 25F:
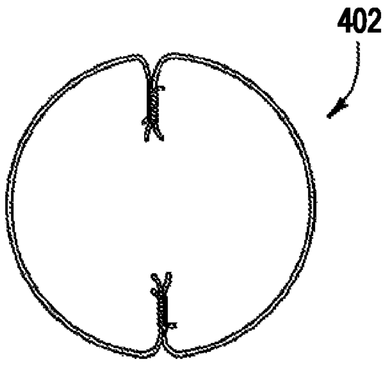

A detailed example of one process path for implant formation is illustrated in FIGS. 25A-25F. As shown in FIG. 25F a final implant 402 may begin as a section 450 of braided material. The tubular braid stock is secured. As shown, it is tied-off with a wire wrap 410. Such action develops an inset region 424 for the implant body. An opposite end of the braid is then captured in a transfer tube 452. The tube is passed through the volume of the implant and secured with a second tie 410 at the other side.

Additional refinement to the shape over that shown in FIG. 25E may be imparted within a shape-setting form 454. Mandrels 456 including stops 458 received through the securement features may be employed to force apposition of the ball to the shape of the form when pulled apart as indicated by arrows. After shape-setting in the form (as appropriate to the selected material—e.g., as in heat setting superelastic Nitinol) the mandrels are removed and the implant shaping is complete as shown in FIG. 25F. However, these additional forming steps are not necessary given that (in point of fact) the implant in FIG. 22 was produced without employing the same.

Methods of Use

Any one of the subject implants is delivered to a target site employing known percutaneous catheter access techniques. The implant may be secured to a pusher (e.g., pusher 430) used to advance it through the access catheter (e.g., microcatheter 444). Upon emplacement at the treatment site (e.g., cerebral aneurysm 426 as illustrated in FIG. 23A), the implant can be detached. With the exemplary system shown in FIG. 24, the suture 440 passing through the proximal end of the implant 402 is severed by melting it using a resistance heater. This retention/release fiber remains in and with the implant.

We claim:

1. An embolic device for treatment of an aneurysm of a patient's vasculature, the device comprising:

a braid configured to be positioned within a cavity of the aneurysm, the braid having an interior volume and comprising a plurality of woven filaments that are secured relative to each other at proximal and distal end portions of the braid to form respective proximal and distal hubs, the braid having an intermediate portion between the proximal and distal end portions, wherein the proximal and distal hubs are disposed exterior to the interior volume and are inset towards the interior volume; and wherein the embolic device comprises (i) a radially constrained state configured for delivery through an elongate shaft in which the braid has a first length, and (ii) an expanded state in which the braid has a second length less than the first length, wherein the embolic device is configured to assume the expanded state when released from the elongate shaft and positioned within the cavity of the aneurysm, and wherein, in the expanded state, the entire braid has a generally globular shape such that a diameter of the braid increases towards the intermediate portion of the braid and decreases towards the proximal and distal end portions of the braid.

2. The embolic device of claim 1, wherein the braid is a single layer.

3. The embolic device of claim 1, wherein the plurality of woven filaments includes first filaments having a first diameter and second filaments having a second diameter different than the first diameter.

4. The embolic device of claim 1, wherein the braid is self-expanding.

5. The embolic device of claim 1, wherein the braid comprises a plurality of openings between each of the plurality of filaments.

6. The embolic device of claim 1, wherein the proximal hub includes a radiopaque marker band.

7. The embolic device of claim 1, wherein the distal hub includes a radiopaque marker band.

8. An embolic device for treatment of an aneurysm of a patient's vasculature, the device comprising:

a single-layer braided structure configured to be positioned within a cavity of the aneurysm, the braided structure comprising an interior volume surrounded by a plurality of wires that are secured relative to each other at proximal and distal end portions of the structure to form respective proximal and distal hubs, the proximal and distal hubs disposed exterior to the interior volume; and wherein, the braided structure comprises an expanded shape comprising a proximal end portion, a distal end portion, and intermediate portion extending therebetween, wherein the intermediate portion is concave towards the interior volume and the distal and proximal end portions are convex towards the interior volume, such that the proximal and distal hubs are inset into the interior volume, and wherein a diameter of the braided structure increases towards the intermediate portion and decreases towards the proximal and distal end portions of the braided structure such that the interior volume is generally spherical.

9. The embolic device of claim 8, wherein at least some of the wires comprise a shape-memory alloy.

10. The embolic device of claim 9, wherein at least some of the wires comprise a superelastic material.

11. The embolic device of claim 9, wherein at least some of the wires are drawn-filled tubes having a platinum core surrounded by an outer layer of Nitinol.

12. The embolic device of claim 9, wherein at least some of the wires are drawn-filled tubes having a gold core surrounded by an outer layer of Nitinol.

13. An embolic device for treatment of an aneurysm of a patient's vasculature, the device comprising:

a self-expandable braided structure configured to be positioned within a cavity of the aneurysm, the braided structure comprising a single layer of a plurality of filaments defining an interior volume of the braided structure, wherein the plurality of filaments are secured relative to each other via proximal and distal bands at proximal and distal end portions of the braided structure, respectively, wherein the braided structure comprises (a) a radially constrained state configured for delivery through a microcatheter, and (b) an expanded state in which the braided structure has a generally globular shape between the proximal and distal end portions of the braided structure and is longitudinally shortened relative to the radially constrained state, a diameter of the braided structure increases towards an intermediate portion of the braided structure and decreases towards the proximal and distal end portions of the braided structure, and the proximal and distal bands are inset towards the interior volume, wherein the braided structure is configured to assume the expanded state when released from the microcatheter and positioned within the cavity of the aneurysm; and wherein the plurality of filaments comprises between 96 and 288 filaments and at least some of the plurality of filaments are composite filaments comprising a radiopaque core material surrounded circumferentially by Nitinol.

14. The embolic device of claim 13, wherein the plurality of filaments includes first filaments having a first diameter and second filaments having a second diameter different than the first diameter.

* * * * *